US011286469B2

(12) United States Patent
Raines et al.

(10) Patent No.: US 11,286,469 B2
(45) Date of Patent: Mar. 29, 2022

(54) COMBINATION CHEMOTHERAPY FOR THE TREATMENT OF CANCER

(71) Applicant: Wisconsin Alumni Research Foundation, Madison, WI (US)

(72) Inventors: Ronald T. Raines, Madison, WI (US); Trish Hoang, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 19 days.

(21) Appl. No.: 16/184,629

(22) Filed: Nov. 8, 2018

(65) Prior Publication Data
US 2019/0136212 A1 May 9, 2019

Related U.S. Application Data

(60) Provisional application No. 62/583,759, filed on Nov. 9, 2017.

(51) Int. Cl.
*C12N 9/22* (2006.01)
*A61K 31/519* (2006.01)
*A61P 35/04* (2006.01)

(52) U.S. Cl.
CPC .............. *C12N 9/22* (2013.01); *A61K 31/519* (2013.01); *A61P 35/04* (2018.01); *C12Y 301/27005* (2013.01)

(58) Field of Classification Search
CPC ......... C12N 9/22; A61K 31/519; A61P 35/04; C12Y 301/27005
See application file for complete search history.

(56) References Cited

U.S. PATENT DOCUMENTS

| | | | |
|---|---|---|---|
| 5,840,296 | A | 11/1998 | Raines |
| 6,280,991 | B1 | 8/2001 | Raines |
| 7,416,875 | B2 | 8/2008 | Raines |
| 7,655,757 | B2 | 2/2010 | Raines |
| 7,977,079 | B2 | 7/2011 | Raines |
| 8,048,425 | B2 | 11/2011 | Raines |
| 8,293,872 | B2 | 10/2012 | Raines |
| 8,524,480 | B2 | 9/2013 | Raines |
| 8,569,457 | B2 | 10/2013 | Raines |
| 8,697,062 | B2 | 4/2014 | Raines |
| 8,802,413 | B2 | 8/2014 | Raines |
| 9,234,191 | B2 | 1/2016 | Raines |
| 9,255,260 | B2 | 2/2016 | Raines |
| 2006/0292137 | A1* | 12/2006 | Raines ................... C12N 9/22 424/94.6 |
| 2013/0011904 | A1* | 1/2013 | Raines ................... A61P 43/00 435/199 |

OTHER PUBLICATIONS

Whisstock et al. Quaterly Reviews of Biophysics, 2003, "Prediction of protein function from protein sequence and structure", 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36):11643-50.*
Rex Wayne Watkins, Improvements to fluorescent affinity labels and the ribonuclease system and gene expression response to clinically relevant ribonucleases. Dissertation & Theses, Doctor of Philosophy, University of Wisconsin-Madison, 2010, p. 1-155.*
Bhagavathula et al. Rosiglitazone inhibits proliferation, motility and matrix metalloproteinase production in keratinocyte. J Invest Dermatol 122:130-139, 2004.*
Ardelt et al. Onconase and Amphinase, the antitumor ribonuclease from Rana pipiens oocytes. Curr Pharm Biotechnol. 2008; 9(3): 215-225.*
Mironova et al. The systemic tumor response to RNase A treatment affects the expression of genes involved in maintaining cell malignancy. Oncotarget, 2017, Epub Aug. 12, 2017, 8(45): 7896-78810.*
Tran et al. MEK inhibitors and their potential in the treatment of advanced melanoma: the advantages of combination therapy. Drug Design, Development and Therapy 2016:10 43-52.*
Meier et al. Combined targeting of MAPK and AKT signaling pathways is a promising strategy for melanoma treatment. British Journal of Dermatology 2007 156, pp. 1204-1213.*
Anjum et al. (2008) The RSK family of kinases: Emerging roles in cellular signalling. Nat. Rev. Mol. Cell Biol 9:747-758.
Ardelt et al. (2009). Ribonucleases as potential modalities in anticancer therapy. Eur. J. Pharmacol. 625:181-189.
Beintema et al. (1988). Molecular evolution of the ribonuclease superfamily. Prog. Biophys. Molec. Biol. 51:165-192.
Blázquez et al. (1996). Oxidation of sulfhydryl groups of ribonuclease inhibitor in epithelial cells is sufficient for its intracellular degradation. J. Biol. Chem. 271:18638-18642.
Blom et al. (1999) Sequence and structure-based prediction of eukaryotic protein phosphorylation sites. J Mol. Biol. 294:1351-1362.
Blom et al. (2004). Prediction of post-translational glycosylation and phosphorylation of proteins from the amino acid sequence. Proteomics 4:1633-1649.
Boschelli et al. (2001). Optimization of 4-phenylamino-3-quinolinecarbonitriles as potent inhibitors of Src kinase activity. J. Med. Chem. 44:3965-3977.
Chao et al. (2010). Cellular uptake of ribonuclease A relies on anionic glycans. Biochemistry 49:10666-10673.
Chao et al. (2011). Mechanism of ribonuclease A endocytosis: Analogies to cell-penetrating peptides. Biochemistry 50:8374-8382.
Cohen (2000) The regulation of protein function by multisite phosphorylation—a 25 year update Trends Biochem. Sci. 25:596-601.
Dancey et al. (2006). Strategies for optimizing combinations of molecularly targeted anticancer agents. Nat. Rev. Drug Discov. 5:649-659.
Dhillon et al. (2007). MAP kinase signalling pathways in cancer. Oncogene 26:3279-3290.
Dickson et al. (2005). Ribonuclease inhibitor: Structure and function. Prog. Nucleic Acid Res. Mol. Biol. 80:349-374.

(Continued)

*Primary Examiner* — Iqbal H Chowdhury
(74) *Attorney, Agent, or Firm* — Quarles & Brady LLP

(57) ABSTRACT

The present disclosure provides compositions, methods and kits for the treatment of cancer. Particularly, the present disclosure provides synergistic compositions comprising at least one cytotoxic ribonuclease and at least one MAPK-pathway inhibitor.

26 Claims, 16 Drawing Sheets
(16 of 16 Drawing Sheet(s) Filed in Color)
Specification includes a Sequence Listing.

(56) References Cited

OTHER PUBLICATIONS

Dickson et al. (2009). Ribonuclease inhibitor regulates neovascularization by human angiogenin. Biochemistry 48:3804-3806.
Dunn et al. (2005). The Ras-MAPK signal transduction pathway, cancer and chromatin remodeling. Biochem. Cell Biol. 83:1-14.
Fang et al. (2011). Ribonucleases of different origins with a wide spectrum of medicinal applications. Biochim. Biophys. Acta 1815:65-74.
Ferreras et al. (1995). Thiol-disulfide exchange of ribonuclease inhibitor bound to ribonuclease A. J. Biol. Chem. 270:28570-28578.
Fett et al. (1985). Isolation and characterization of angiogenin, an angiogenic protein from human carcinoma cells. Biochemistry 24:5480-5486.
Fisher et al. (1998). A new remote subsite in ribonuclease A. J. Biol. Chem. 273:34134-34138.
Fominaya et al. (1992). Inactivation of ribonuclease inhibitor by thiol-disulfide exchange. J. Biol. Chem. 267:24655-24660.
Fontecilla-Camps et al. (1994). Crystal structure of ribonuclease A-d(ApTpApApG) complex. J. Biol. Chem. 269:21526-21531.
Fry et al. (2004). Specific inhibition of cyclin-dependent kinase 4/6 by PD 0332991 and associated antitumor activity in human tumor xenografts. Mol. Cancer Ther. 3:1427-1438.
Gibson et al. (2009). Enzymatic assembly of DNA molecules up to several hundred kilobases. Nat. Methods 6:343-345.
Greger et al. (2012). Combinations of BRAF, MEK, and PI3K/mTOR inhibitors overcome acquired resistance to the BRAF inhibitor GSK21 18436 dabrafenib, mediated by NRAS or MEK mutations. Mol. Cancer Ther. 11:909-920.
Haigis et al. (2002). Evolution of ribonuclease inhibitor protein by exon duplication. Mol. Biol. Evol. 19:960-964.
Hoang et al. (2017). Molecular basis for the autonomous promotion of cell proliferation by angiogenin. Nucleic Acids Res. 45:818-831.
Hofsteenge (1997). Ribonuclease inhibitor. In Ribonucleases: Structures and Functions, D'Alessio G, Riordan JF (eds) pp. 621-658. New York: Academic Press.
Johnson (2009). The regulation of protein phosphorylation. Biochem. Soc. Trans. 38 (Part4):627-641.
Johnson et al. (2007). Inhibition of Human Pancreatic Ribonuclease by the Human Ribonuclease Inhibitor Protein, Journal of Molecular Biology, vol. 368, Issue 2, pp. 434-449, ISSN 0022-2836.
Kajava (1998). Structural diversity of leucine-rich repeat proteins. J. Mol. Biol. 277:519-527.
Kam et al. (2008). Flat-bottom strategy for improved accuracy in protein side-chain placements. J. Chem. Theor. Comput. 4:2160-2169.
Kefford et al. (2010). Phase I/II study of GSK2118436, a selective inhibitor of oncogenic mutant BRAF kinase, in patients with metastatic melanoma and other solid tumors. J. Clin. Oncol. 28 Suppl.:8503.
Kim et al. (1999). Variants of ribonuclease inhibitor that resist oxidation. Protein Sci. 8:430-434.
King et al. (2013). Dabrafenib; preclinical characterization, increased efficacy when combined with trametinib, while BRAF/MEK tool combination reduced skin lesions. PLoS ONE 8:e67583.
Knight et al. (2005). Features of selective kinase inhibitors. Chem. Biol. 12:621-637.
Knight et al. (2010). Targeting the cancer kinome through polypharmacology. Nat. Rev. Cancer 10:130-137.
Kobe et al. (1993). Crystal structure of porcine ribonuclease inhibitor, a protein with leucine-rich repeats. Nature 366:751-756.
Kobe et al. (1995). A structural basis of the interactions between leucine-rich repeats and protein ligands. Nature 374:183-186.
Kolch et al. (1993). Protein kinase Cα activates RAF-1 by direct phosphorylation. Nature 364:249-252.
Kong et al. (2017). Cancer drug addition is related by an ERK2-dependent phenotype switch. Nature 550:270-274.
Lee et al. (1993). Structure and action of mammalian ribonuclease (angiogenin) inhibitor. Prog. Nucleic Acid Res. Mol. Biol. 44:1-30.
Li et al. (2014). Ribonuclease inhibitor up-regulation inhibits the growth and induces apoptosis in murine melanoma cells through repression of angiogenin and ILK/PI3K/AKT signaling pathway Biochimie 103:89-100.
Lim et al. (1997). Molecular dynamics for very large systems on massively parallel computers: The MPSim program. J. Comput. Chem. 18:501-521.
Lite et al. (2016). Allele-specific inhibitors inactivate mutant KRAS G12C by a trapping mechanism. Science 351:604-608.
Lomax et al. (2012). Rational design and evaluation of mammalian ribonuclease cytotoxins. Methods Enzymol. 502:273-290.
Lomax et al. (2014). Functional evolution of ribonuclease inhibitor: Insights from birds and reptiles. J. Mol. Biol. 26:3041-3056.
Lomax et al. (2017). Comparative functional analysis of ribonuclease 1 homologs: Molecular insights into evolving vertebrate physiology. Biochem. J. 474:2219-2233.
Long et al. (2015). Dabrafenib and trametinib versus dabrafenib and placebo for Val600 BRAF-mutant melanoma: A multicentre, double-blind, phase 3 randomised controlled trial. Lancet 386:444-451.
Long et al. (2017). Adjuvant dabrafenib plus trametinib in stage III BRAF-mutated melanoma. N. Eng. J. Med.:In Press; DOI: 10.1056/NEJMoa1708539.
Lopez et al. (2016). Combine and conquer: Challenges for targeted therapy combinations in early phase trials. Nat. Rev. Clin. Oncol. 14:57-66.
Lovell et al. (1999). Asparagine and glutamine: Using hydrogen atom contacts in the choice of side-chain amide orientation. J. Mol. Biol. 285:1735-1747.
Lugowska et al. (2015). Trametinib: A MEK inhibitor for management of metastatic melanoma. Onco. Targets. Ther. 8:2251-2259.
Lyons et al. (2017). RNA biology of angiogenin: Current state and perspectives. RNA Biol. 14:171-178.
Mayo et al. (1990). Dreiding: A generic force field for molecular simulations. J. Phys. Chem. 94:8897-8909.
McCubrey et al. (2007). Roles of the Raf/MEK/ERK pathway in cell growth, malignant transformation and drug resistance. Biochim. Biophys. Acta 1773:1263-1284.
Moroianu et al. (1994). Nuclear translocation of angiogenin in proliferating endothelial cells is essential to its angiogenic activity. Proc. Natl. Acad. Sci. U.S.A. 91:1677-1681.
Ostrem et al. (2016). Direct small-molecule inhibitors of KRAS: From structural insights to mechanism-based design. Mat. Rev. Drug Discov. 15:771-785.
Papageorgiou et al. (1997). Molecular recognition of human angiogenin by placental ribonuclease inhibitor—an X-ray crystallographic study at 2.0 Å resolution. EMBO J. 16:5162-5177.
Patricelli et al. (2016). Selective inhibition of oncogenic KRAS output with small molecules targeting the inactive state. Cancer Discov. 6:316-329.
Pirotte et al. (1952). Distribution de la ribonuclease dans les extrait de granules cellulaire du foie. Bull. Soc. Chim. Belg. 61:167-180.
Pizzo et al. (2007). The success of the RNase scaffold in the advance of biosciences and in evolution. Gene 406:8-12.
Poole (2015). The basics of thiols and cysteines in redox biology and chemistry. Free Radic. Biol. Med. 80:148-157.
Raines (1998). Ribonuclease A. Chem. Rev. 98:1045-1065.
Roberts et al. (2007). Targeting the Raf-MEK-ERK mitogen-activated protein kinase cascade for the treatment of cancer. Oncongene 26:3291-3310.
Roskoski (2012). MEK1/2 dual-specificity protein kinases: Structure and regulation. Biochem. Biophys. Res. Commun. 417:5-10.
Roth (1953). Effect of sulphydryl reactants on liver ribonuclease. Nature 171:127-128.
Roth (1956). Studies on the properties and distribution of ribonuclease inhbitor in the rat. Biochim. Biophys. Acta 21:34-43.
Rutkoski et al. (2008). Evasion of ribonuclease inhibitor as a determinant of ribonuclease cytotoxicity. Curr. Pharm. Biotechnol. 9:185-189.
Samatar et al. (2014). Targeting RAS-ERK signalling in cancer: Promises and challenges. Nat. Rev. Drug Discov. 13:928-942.
Shapiro et al. (1987). Human placental ribonuclease inhibitor abolishes both angiogenic and ribonucleolytic activities of angiogenin. Proc. Natl. Acad. Sci. U.S.A. 84:2238-2241.

(56) References Cited

OTHER PUBLICATIONS

Shaul et al. (2007). The MEK/ERK cascade: From signaling specificity to diverse functions. Biochim. Biophys. Acta 1773:1213-1226.
Strong et al. (2012). First in human phase I clinical trial of QBI-139, a human ribonuclease variant, in solid tumors. J. Clin. Oncol. 30 (Suppl.):TPS3113.
Strong et al. (2012). Efficacy of ribonuclease QBI-139 in combination with standard of care therapies. Cancer Res. 72 (Suppl. 1):1838.
Thomas et al. (2016). Knockout of the ribonuclease inhibitor gene leaves human cells vulnerable to secretory ribonucleases. Biochemistry 55:6359-6362.
Torii et al. (2006). Erk Map kinase in G cell cycle progression and cancer. Cancer Sci. 97:697-702.
Vlastaridis et al. (2017). Estimating the total number of phosphoprotines and phosphorylation sites in eukaryotic proteomes. GigaScience 6:1-11.
Xu et al. (2002). The nuclear function of angiogenin in endothelial cells is related to rRNA production. Biochem. Biophys Res Commun. 294:287-292.
Yamaguchi et al. (2011). Antitumor activities of JTP-74057 (GSK1120212), a novel MEK1/2 inhibitor, on colorectal cancer cell lines in vitro and in vivo. Int. J. Oncol. 39:23-31.
Yap et al. (2011) Small molecule inhibitors of the ERK signaling pathway: Towards novel anti-cancer therapeutics. ChemMedChem 6(1):38-48.
Zou et al. (2007). An orally available small-molecule inhibitor of c-Met, PF-2341066, exhibits cytoreductive antitumor efficacy through antiproliferative and antiangiogenic mechanisms. Cancer Res. 67:4408-4417.
Haigis et al. (2003) Ribonuclease inhibitor as an intracellular sentry, 1024-1032, Nulceic Acids Research, 2003, vol. 31, No. 3.

* cited by examiner

Phosphorylation of Thr81

Phosphorylation of Ser177

Phosphorylation of Ser289

Phosphorylation of Ser382

Phosphorylation of Ser405

| Cell Line | $EC_{50}$ (nM) | | |
|---|---|---|---|
| | Trametinib | Dabrafenib | ptRNAse[a] |
| SK-MEL-28 | 1.2 ± 0.6 | 10.3 ± 1.1 | 8.9 ± 1.1 |
| A375 | 0.8 ± 0.1 | 9.7 ± 0.7 | 11.9 ± 1.2 |
| Malme-3M | 0.15 ± 0.06 | 4.3 ± 0.6 | 4.7 ± 0.8 |
| Malme-3 | >1000[b] | >1000[b] | 27.5 ± 2.6 |

[a]Values (± SE) are for cell viability as measured with a tetrazolium dye-based assay for metabolic activity.
[b]A concentration of >1000 nM resulted in >75% cell viability.

FIG. 11
```
         Ser177          Ser289          Ser405
Human    KELTVSNNDINE...SLKELSLAGNEL...RELDLSNNCLGD  (SEQ ID NO:2)
Mouse    KELVLSNNDLHE...SLKELSLASNEL...RELDLSNNCMGG  (SEQ ID NO:3)
Rat      KELVLSNNDFHE...SLKELSLAGNEL...RELDLSNNCMGD  (SEQ ID NO:4)
Pig      KELTVSNNDIGE...TLKELSLAGNKL...RELDLSNNCVGD  (SEQ ID NO:5)
```
FIG. 12
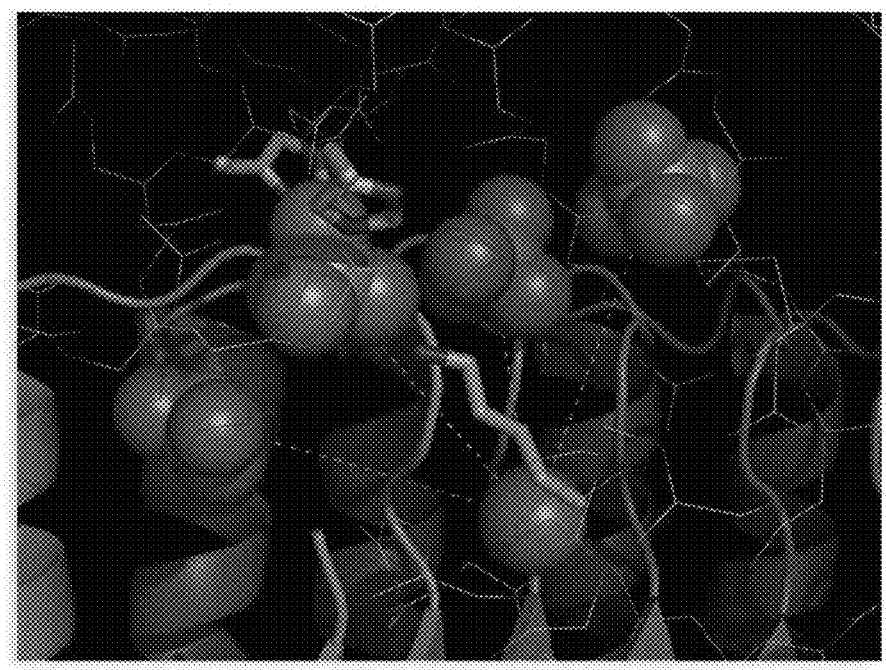
FIGS. 13A-13B
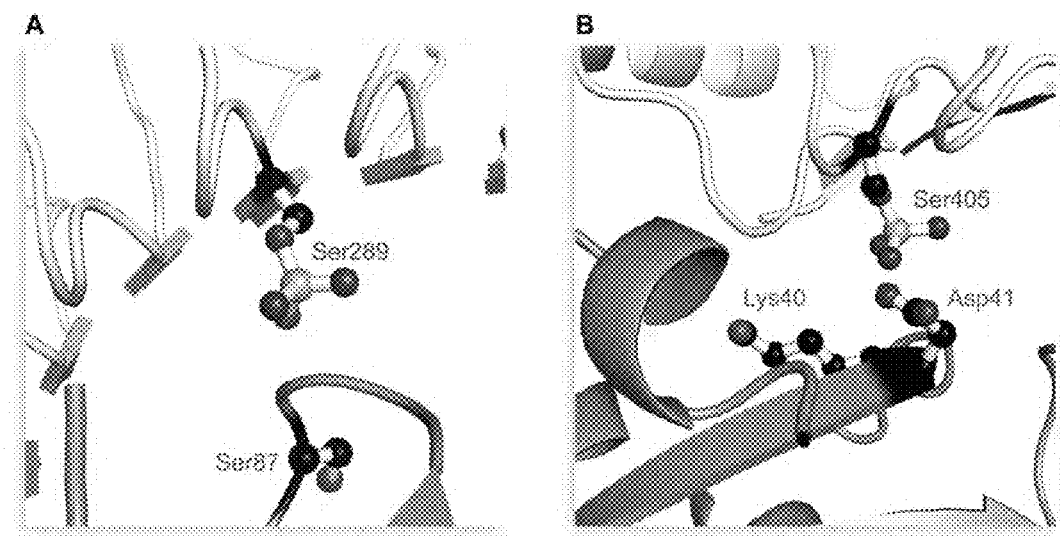

COMBINATION CHEMOTHERAPY FOR THE TREATMENT OF CANCER

CROSS-REFERENCE TO RELATED APPLICATIONS

This application claims priority to U.S. Provisional Application No. 62/583,759 filed on Nov. 9, 2017, the contents of which are incorporated by reference in its entirety.

STATEMENT REGARDING FEDERALLY SPONSORED RESEARCH

This invention was made with government support under CA073808 awarded by the National Institutes of Health. The government has certain rights in the invention.

BACKGROUND OF THE INVENTION

The field of the invention is related to combination therapy compositions for the treatment of cancer and methods of use. Specifically, the invention relates to protein kinase inhibitors in combination with pancreatic-type ribonucleases (ptRNases).

The phosphorylation of proteins by kinases regulates critical intracellular processes (Cohen, 2000; Johnson, 2009). Within human cells, a key signaling cascade is manifested by phosphorylation in the Ras-Raf-MEK-ERK pathway (Shaul and Seger, 2007; Samatar and Poulikakos, 2014). The binding of growth factors to extracellular receptors activates Ras, which in turn activates the protein kinase activity of Raf kinase (Ostrem and Shokat, 2016). Raf kinase catalyzes the phosphorylation of MEK, and MEK catalyzes the phosphorylation of ERK (Roskoski, 2012). ERK has more than 400 substrates, including p90 ribosomal S6 kinase-1 (RSK) (Anjum and Blenis, 2008), and its kinase activity regulates gene expression related to cell growth and proliferation.

Ribonuclease inhibitor (RI) is a 50-kDa cytosolic protein found in all mammalian cells (Dickson et al., 2005), and is not known to undergo phosphorylation (Vlastaridis et al., 2017). Human RI is composed of 15 leucine-rich repeats that endow the protein with the shape of a horseshoe (Kobe and Deisenhofer, 1993; Kajava, 1998), which is conserved in homologs (Lomax et al., 2014). RI has an atypical abundance of cysteine residues, which are necessarily in a reduced state in the folded protein (Blázquez et al., 1996; Kim et al., 1999). Twenty-seven of the 32 cysteine residues of human RI are conserved in mice, pigs, and rats, suggesting a role in function (Lomax et al., 2014). The cytosolic concentration of RI is ~4 nM (Haigis et al., 2003). This relatively high concentration, coupled with the ubiquitous expression of its mRNA in mammalian tissues, is consistent with an important role.

RI is known to act as a "sentry" that protects mammalian cells from pancreatic-type ribonucleases (ptRNases) (Haigis et al., 2003; Thomas et al., 2016). These ribonucleases are secretory but can enter cells via endocytosis. A fraction of the protein escapes from endosomes into the cytosol but is then inhibited by RI (Chao et al., 2010; Chao and Raines, 2011). A ptRNase that is resistant to RI can degrade cellular RNAs, resulting in apoptosis (Rutkoski and Raines, 2008; Lomax et al., 2012). Such RI-evasive homologs and variants have shown promise as cancer chemotherapeutic agents (Ardelt et al., 2009; Fang and Ng, 2011). Surprisingly, RI has not been found to interact with any intracellular protein, consistent with a functional rote in regulating invading ptRNases.

Typical RI•ptRNase complexes have $K_d$ values in the femtomolar range (Dickson et al., 2005; Lomax et al., 2012), making the RI-ptRNase interaction the tightest known between biomolecules. The RI•ptRNase complex is stabilized by favorable Coulombic interactions, as RI is highly anionic and ptRNases are highly cationic (Kobe and Deisenhofer, 1995; Papageorgiou et al., 1997; Johnson et al., 2007; Lomax et al., 2014). To date, however, all detailed analyses of RI have been performed on protein produced by heterologous expression in *Escherichia coli*. Understanding the characterization and cellular processes of RI may improve understanding for treatment uses of such compositions, including the use for cancer treatment.

There is a need for new therapeutic combinations that can specifically treat cancers.

SUMMARY OF THE INVENTION

The present invention provides a combination therapy for treatment of cancer comprising at least one cytotoxic ribonuclease and at least one ERK-pathway (or, equivalently, MAPK-pathway) inhibitor.

In one aspect, the disclosure provides a synergistic composition for the treatment of cancer, the composition comprising at least one MAPK-pathway inhibitor and at least one cytotoxic ribonuclease.

In some aspects, the at least one MAPK-pathway inhibitor is selected from a MEK inhibitor, an ERK inhibitor, a RAF inhibitor, and a RAS inhibitor.

In some aspects, the cancer comprises a cancer or tumor having cells that exhibit ERK pathway activation or cells that exhibit up-regulation of the RAF-MEK-ERK pathway.

In further aspects, the ERK pathway activation in the cancer can result from a mutation in KRAS; a mutation in NRAS; a mutation in HRAS; a mutation in ARAF; a mutation in BRAF; a mutation in CRAF; a mutation in MAP2K1 (MEK1); loss of NF1 function due to mutation, deletion, and/or promoter methylation; activation of RAS by cell-surface receptors; or activation of RAF by other kinases such as PKC alpha (Kolch et al., 1993).

In another aspect, the disclosure provides a method of treating cancer in a subject comprising administering to the subject a therapeutically effective amount of the composition comprising at least one MAPK-pathway inhibitor and at least one cytotoxic ribonuclease.

In some aspects, the administration of the composition results in synergistic inhibition or reduction of cancer growth.

In yet another aspect, the disclosure provides a method of reducing or inhibiting cancer cell growth in a subject having cancer, the method comprising administering an effective amount of the synergistic composition comprising at least one MAPK-pathway inhibitor and at least one cytotoxic ribonuclease, wherein cancer cell growth is reduced or inhibited in the subject.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 11 demonstrates the conservation of phosphorylated residues of mammalian RI. Phosphoryl groups on these residues interact favorably with a ptRNase (FIG. 1E).

FIG. 12 shows the proximity of a phosphoryl group on Ser405 of RI to the phosphoryl group-binding subsites in an RI•ptRNase complex. The image shows the superposition of the RNase A•d(ATAAG) complex (PDB entry 1rcn) on the RNase complex (PDB entry 1z7x). RI is depicted as a gray ribbon; RNase 1 is depicted as lines with its three active-site residues (His12, Lys41, and His119) depicted as sticks. Only the phosphoryl groups from PDB entry 1rcn are shown. A phosphoryl group was installed computationally on $O^\gamma$ of Ser405; for clarity, only its phosphorus atom is shown. Phosphorus atoms are shown as orange spheres. Dashed lines depict distances, which are as short as 8.5 Å. The image was made with the program PyMOL from Schrödinger (New York, N.Y.).

FIGS. 13A-13B show models of the effect of RI phosphorylation on its affinity for ANG. (A and B) Images showing the proximity of a phosphoryl group on Ser289 of RI (panel A) or Ser405 of RI (panel B) to key residues of ANG in the RI•ANG complex. RI is depicted as a gray ribbon; ANG is depicted as a green ribbon. Ser87 is phosphorylated in ANG (Hoang and Raines, 2017). A phosphoryl group was installed computationally on $O^\gamma$ of the two serine residues of RI. The image was made with PDB entry 1a4y and the program PyMOL.

DETAILED DESCRIPTION OF THE INVENTION

Figures 4A, 4B, 4C, 4D:
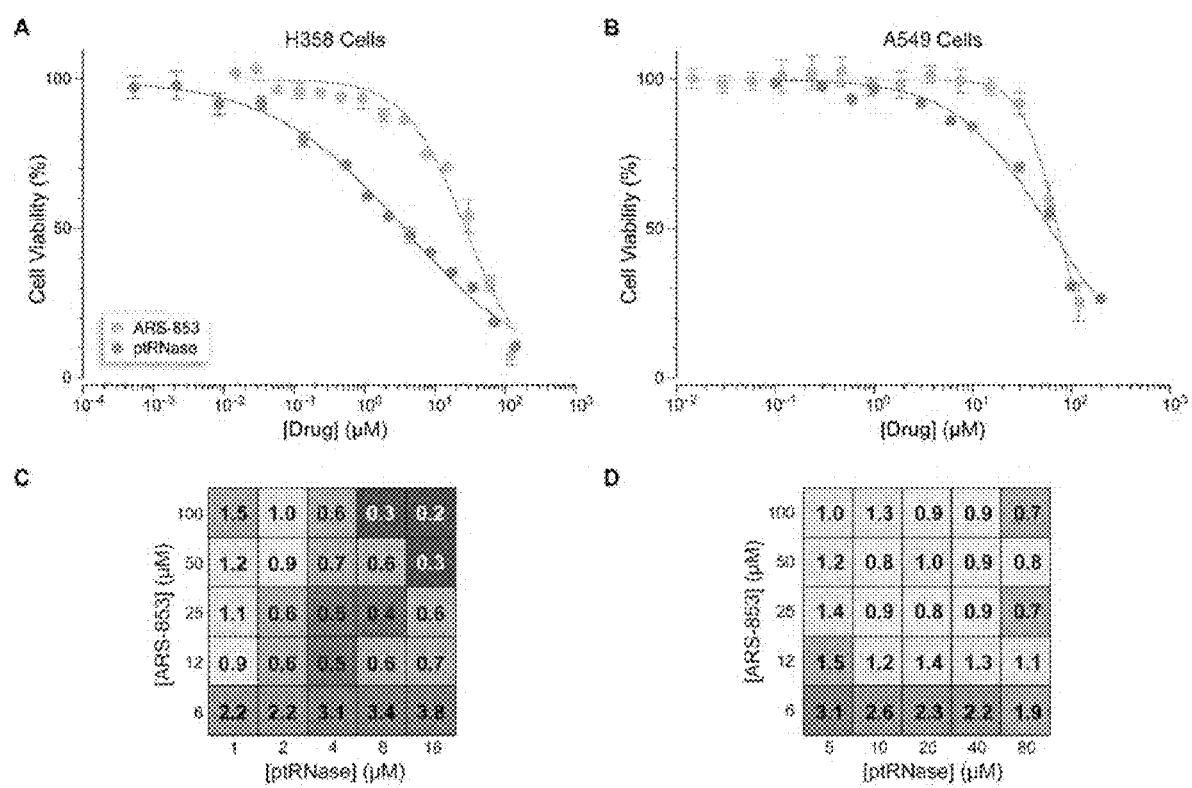
FIGS. 4A-4D show the inhibition of ERK pathway enhances the toxicity of the ptRNase for human lung cancer cells. (A) the ptRNase is more toxic to 1-1358 cells (EC50=3.6±0.6 µM), which harbor the $KRAS^{G12C}$ substitution, than is ARS-853 (EC50=28±4 µM). Values represent the mean±SEM (n=3, biological replicates). (B) the ptRNase and ARS-853 have indistinguishable toxicity for A549 cells (EC50=62±7 µM and EC50=74±8 µM, respectively). Data for the toxicity of the ptRNase are from FIG. 4A. Values represent the mean±SEM (n=3, biological replicates). (C, D) Synergistic effects of ARS-853 and the ptRNase. The combination exerts greater synergism against H358 cells than against A549 cells.
Figures 5A, 5B, 5C:
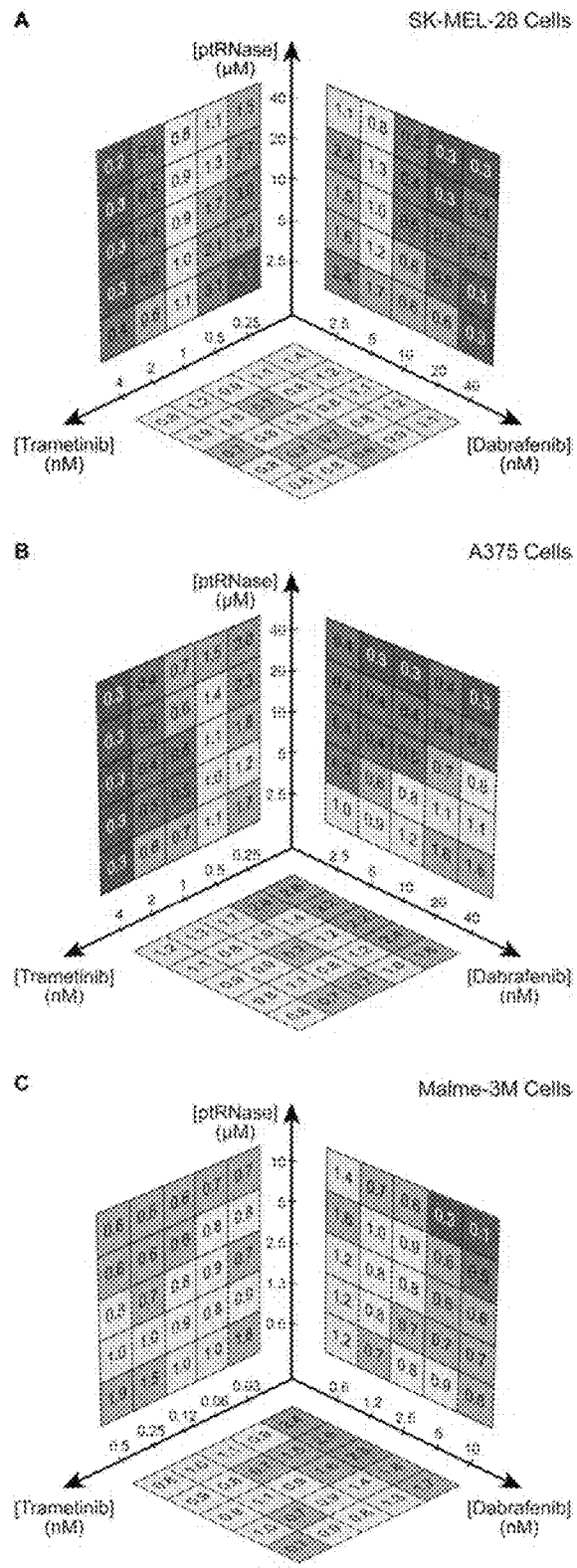
FIGS. 5A-5C demonstrates the synergistic effects of the combined treatment of kinase inhibitors and the ptRNase on human melanoma cells. The combination of dabrafenib and the ptRNase exerts greater synergism than does the combination of trametinib and the ptRNase across 3 different melanoma cell lines: SK-MEL-28 cells (A), A375 cells (B), and Malme-3M cells (C). Treatment with the two kinase inhibitors without ptRNAase, trametinib and dabrafenib, results in additive effects. Values represent the mean±SEM (n=3, biological replicates).

The present invention relates to synergistic compositions for the treatment of cancer. Specifically, the present invention provides synergistic compositions comprising at least one MAPK-pathway inhibitor and at least one cytotoxic ribonuclease (e.g., a pancreatic-type ribonuclease (ptRNase) variant) in which the composition provides a synergistic effect in the treatment of cancer. As described in the examples below, the inventors unexpectedly found that the combination of a cytotoxic ribonuclease with at least one MAPK-pathway inhibitor resulted in a synergistic increase in the ability of the cytotoxic ribonucleases to kill cancer cells. As shown in FIGS. 4 and 5, the combination of a cytotoxic ribonuclease and different MAPK-pathway inhibitors (e.g., MEK inhibitor, KRAS inhibitor, BRAF inhibitor) showed synergistic tumor cell killing when compared to the MAPK-pathway inhibitors alone or in combination with each other. This invention provides compositions for and methods of treating cancer combining at least one cytotoxic ribonuclease with at least one MAPK-pathway inhibitor.

In one embodiment, the present disclosure provides a synergistic composition comprising at least one cytotoxic ribonuclease and at least one MAPK-pathway inhibitor. In another embodiment, the synergistic composition comprises at least one cytotoxic ribonuclease and two or more MAPK-pathway inhibitors.

Suitable cytotoxic ribonucleases for use in the present invention include human variants of pancreatic-type ribonuclease (ptRNase). These ptRNases have been modified to retain ribonucleolytic activity and have a lower binding affinity for RI than that of the native ptRNase. ptRNases that have been modified to be RI-resistant can be used in the present invention. Suitable cytotoxic ribonucleases can be found in U.S. Pat. Nos. 5,840,296; 6,280,991; 7,655,757; 7,416,875; 7,977,079; 8,524,480; 8,697,062; 8,802,413; 9,255,260; 8,048,425; 8,293,872; 8,569,457; and 9234191, the contents of which are incorporated by reference in their entirety. In one embodiment, the cytotoxic ribonuclease is a ptRNase which is a human RNase 1 variant that is engineered or chemically modified to bind with lower affinity to RI than the wild-type RNase 1. Suitable examples of such modification of human ptRNase (RNase 1, protein sequence found in SEQ ID NO:1 and nucleic acid sequence found in GenBank CAG29314.1) include:

G38R/R39G/N67R/N88R RNase 1
R39D/N67D/N88A/G89D/R91D RNase 1
R39L/N67L/N88A/G89L/R91L RNase 1
N67D/N88A/G89D/R91D RNase 1
R39D/N88A/G89D/R91D RNase 1
R39D/N67D/G89D/R91D RNase 1
R39D/N67D/N88A/R91D RNase 1
R39D/N67D/N88A/G89D RNase 1
R4C/G38R/R39D/L86E/N88R/G89D/R91D/V118C RNase 1
R4C/G38R/R39G/N67R/G89R/S90R/V118C RNase 1
R4C/G38R/R39G/G89R/S90R/V118C RNase 1
R4C/G38R/R39G/E49R/D53R/N67R/G89R/S90R/V118C RNase 1, and
R4C/G38R/R39G/E49R/D53R/N67R/L86E/N88R/G89D/R91D/V118C RNase 1.

These ptRNases have been tested and shown to have lower binding affinity for RI as compared to the wildtype ptRNase. Suitable ptRNases can be found in Johnson et al. (Inhibition of Human Pancreatic Ribonuclease by the Human Ribonuclease Inhibitor Protein, Journal of Molecular Biology, Volume 368, Issue 2, 2007, Pages 434-449, ISSN 0022-2836, //doi.org/10.1016/j.jmb.2007.02.2005.), the contents of which are incorporated by reference in its entirety.

The term "MAPK pathway" used herein refers to the MAPK/ERK pathway (also known as the Ras→Raf→MEK (mitogen-activated kinase kinase)→ERK (extracellular-signal-regulated kinase) signaling pathway), which controls several fundamental cellular processes, driving proliferation, differentiation, and cell survival. Signal transduction through this pathway is activated by a number of different ligands. In normal cells, RAS activates RAF kinases which in turn phosphorylate and activate MEK1 and MEK2, which upon activation phosphorylate ERK1 and ERK2. ERK regulates the activity and expression of multiple nuclear transcription factors and cytosolic proteins needed for cell proliferation, differentiation and survival. There are a number of mutations and alternations in the MAPK pathway proteins that de-regulate the pathway in numerous human cancers, allowing for cell survival and proliferation of the cancer or tumor cells. The MAPK inhibitors of the present invention result in the inhibition of ERK activation which in turn leads to reduced cellular growth and ultimately cell death.

Suitable examples of MAPK pathway inhibitors for use in the present invention include, but are not limited to, for example, a MEK inhibitor, an ERK inhibitor, a BRAF inhibitor, a KRAS inhibitor, RAF inhibitors and PKC inhibitors. In preferred embodiments, the MAPK pathway inhibitor is a MEK inhibitor, an ERK inhibitor, a BRAF inhibitor, a KRAS inhibitor or combinations thereof. For example, suitable inhibitors that are available from Sellechchem (Boston, Mass.) or other companies are listed in Table 2.

In some embodiments, the MAPK-pathway inhibitor is a RAF inhibitor. In some embodiments, the MAPK-pathway inhibitor is a pan-RAF inhibitor. In some embodiments, the MAPK-pathway inhibitor is a selective RAF inhibitor. In some embodiments, RAF inhibitor includes, but is not limited to, for example RAF265, sorafenib, dabrafenib (GSK2118436), 5B590885, PLX 4720, PLX4032, GDC-0879 and ZM 336372. Other suitable RAF inhibitors are listed in Table 2.

In some embodiments, the MAPK-pathway inhibitor is a MEK inhibitor. In some embodiments, the MEK inhibitor includes, but is not limited to, for example, trametinib (GSK1120212), selumetinib, binimetinib, cobinmetinib, PD-325901, CI-1040/PD184352, TAK-733, AZD6244, PD318088, PD98059, PD334581, RDEA119, 6-methoxy-7-(3-morpholin-4-yl-propoxy)-4-(4-phenoxy-phenylamino)-quinoline-3-carbonitrile and 4-[3-chloro-4-(1-methyl-1H-imidazol-2-ylsulfanyl)-phenylamino]-6-methoxy-7-(3-morpholin-4-yl-propoxy)-quinoline-3-carbonitrile, and ARRY-438162. In one embodiment, at least one MAPK-pathway inhibitor is trametinib or selumetinib. Other suitable MEK inhibitors are listed in Table 2.

In some embodiments, the MAPK-pathway inhibitor is a BRAF inhibitor. Suitable BRAF inhibitors are known in the art and include, but are not limited to, dabrafenib (trade name Tafinlar, GSK2118436), sorafenib (BAY43-9006, Nexavar), vemurafenib (PLX4032), PLX 4720, GDC-0879, and LGX818. Other suitable BRAF inhibitors are listed in Table 2.

In some embodiments the MAPK-pathway inhibitor is a KRAS inhibitor. Suitable KRAS inhibitors are known in the art and include, but are not limited to, ARS-853 for lung cancer. Other suitable KRAS inhibitors are listed in Table 2.

In some embodiments, the MAPK-pathway inhibitor is an ERK inhibitor. In some embodiments, the ERK inhibitor is selected from the group consisting of VTX11e, AEZS-131, PD98059, FR180204, and FR148083. Other suitable ERK inhibitors include, but are not limited to, for example, small-molecule inhibitors of ERK pathway, including compounds found in Yap J L, Worlikar S, MacKerell A D, Shapiro P, Fletcher S. Small molecule inhibitors of the ERK signaling pathway: Towards novel anti-cancer therapeutics. *ChemMedChem* 2011; 6(1):38-48. doi:10.1002/cmdc.201000354, incorporated by reference in its entirety. Other suitable ERK inhibitors are listed in Table 2.

The term synergistic refers to the combination of components that act in synergy, e.g., the total effect of the combination of each component is greater than the sum of the individual effects of each component alone. In the present invention, the synergistic effect of the cytotoxic ribonuclease in combination with the MAPK inhibitor is synergistic over each component alone, and is also synergistic over the combination of two or more MAPK inhibitors together which only show an additive effect.

The present compositions may be used to treat cancer. The term "cancer" or "tumor" are used interchangeably herein to refer to uncontrolled cell growth within a subject. The compositions, methods and kits of the present invention may be used to treat any cancer or metastasis thereof. In a preferred embodiment, the cancer comprises a cancer or tumor having cells that exhibit ERK pathway activation or exhibit up-regulation of the RAF-MEK-ERK pathway. In some embodiments, the ERK pathway activation in the cancer can result from a mutation in KRAS, a mutation in NRAS, a mutation in HRAS, a mutation in BRAF, a mutation in MAP2K1 (MEK1), loss of NF1 function due to mutation, deletion, and/or promoter methylation, and activation of RAS by cell surface receptors.

In some embodiments, the selection of the MAPK-pathway inhibitor may be determined by determining if the cancer contains a mutation in a specific MAPK pathway protein, and using a MAPK-pathway inhibitor either directed to the affected MAPK protein or a MAPK protein that is downstream of the affected MAPK protein. In some embodiments, the cancer comprises cells expressing a mutation in at least one of the proteins selected from the group consisting of BRAF, MEK or KRAS.

Figure 7:
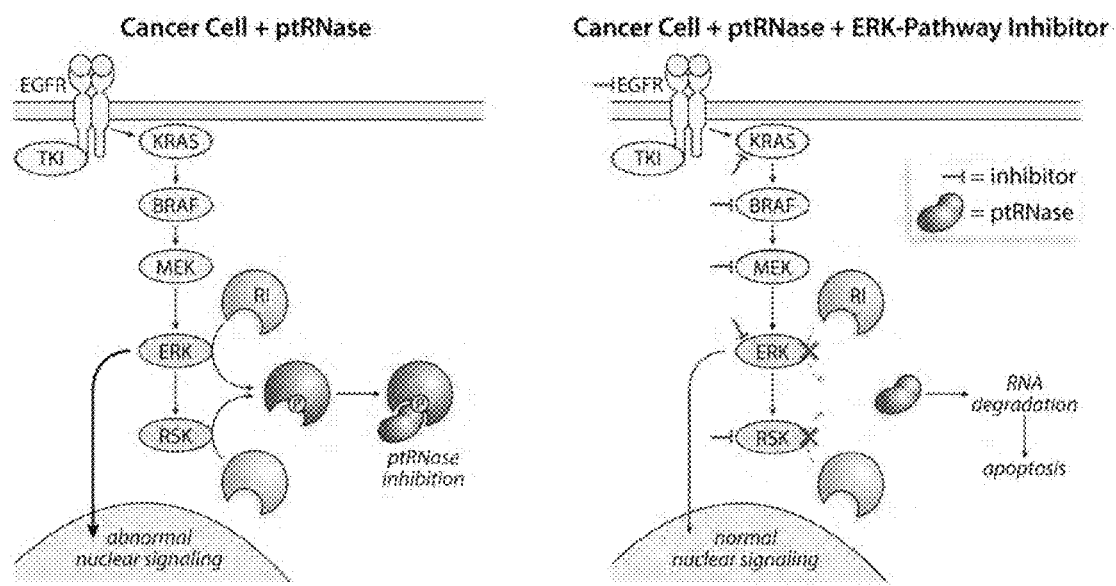
FIG. 7 shows the putative mechanism of synergy between a ptRNase and an ERK-pathway inhibitor. ERK and RSK catalyze the phosphorylation of RI, which strengthens the interaction of RI with an invading ptRNase (left panel). Treatment with an inhibitor diminishes RI phosphorylation and unleashes the ptRNase to manifest its cytotoxic activity (right panel).

For example, in one embodiment, cancer cells having a $BRAF^{V600E/K}$ mutation can be treated with a combination of at least one cytotoxic ribonuclease inhibitor and a MAPK inhibitor which is a BRAF inhibitor, a MEK inhibitor or an ERK inhibitor. The putative mechanism of action and the combination of the six possible points of inhibition in the MAPK pathway that can be combined with the cytotoxic ribonuclease are shown in FIG. 7.

As is known in the art, a cancer is generally considered as uncontrolled cell growth. The methods of the present invention can be used to treat any cancer, any metastases thereof, and any chemo-residual growth thereof, including, but not limited to, carcinoma, lymphoma, blastoma, sarcoma, and leukemia. Suitable cancers able to be treated by the compositions, methods and kits described herein include, but are not limited to, breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma, and peripheral neuroepithelioma. In one embodiment, the cancer is selected from melanoma, non-small cell lung cancer, squamous cell carcinoma of the head and neck, ovarian cancer, pancreatic cancer, renal cell carcinoma, hepatocellular carcinoma, bladder cancer, malignant glioma, colorectal cancer, and endometrial cancer.

In some embodiments, the cancer is a melanoma. In some embodiments, the melanoma is malignant melanoma. In one embodiment, the melanoma is a $BRAF^{V600E/K}$ mutation-positive unresectable or metastatic melanoma.

In another embodiment, the cancer is lung cancer. In one embodiment, the lung cancer comprises cells having a mutation in the KRAS protein. In one embodiment, the lung cancer comprises the KRAS$^{G12C}$ mutation. In one embodiment, the cancer is non-small cell lung cancer.

The terms "metastasis" or "secondary tumor" refer to cancer cells that have spread to a secondary site, e.g., outside of the original primary cancer site. Secondary sites include, but are not limited to, for example, the lymphatic system, skin, distant organs (e.g., liver, stomach, pancreas, brain, etc.), and the like, and will differ depending on the site of the primary tumor.

In a suitable embodiment, the composition comprises the ptRNase and trametinib or dabrafenib.

The compositions described herein may further include a pharmaceutically acceptable carrier. The term "pharmaceutically acceptable carrier" refers any carrier, diluent or excipient that is compatible with the other ingredients of the formulation and not deleterious to the recipient. Pharmaceutically acceptable carrier can be selected on the basis of the selected route of administration and standard pharmaceutical practice for the compounds as described more below.

Methods of Treatment

In some embodiments, the present disclosure provides methods of treating a subject having cancer. In one embodiment, the patient may have metastatic cancer. In another embodiment, the subject may have a melanoma. In some embodiments, the melanoma is malignant melanoma. In one embodiment, the melanoma is a BRAF$^{V600E/K}$ mutation-positive unresectable or metastatic melanoma. In another embodiment, the cancer is lung cancer. In one embodiment, the lung cancer comprises cells having a mutation in the KRAS protein. In one embodiment, the lung cancer comprises the KRAS$^{G12C}$ mutation. In one embodiment, the cancer is non-small cell lung cancer.

Another embodiment provides a method of treating, reducing or inhibiting metastatic cancer growth in a subject, the method comprising administering to the subject a therapeutically effective amount of at least one cytotoxic ribonuclease with at least one MAPK-pathway inhibitor. In some embodiments, the subject is administered a synergistic composition as described above.

For purposes of the present invention, "treating" or "treatment" describes the management and care of a subject for the purpose of combating the disease, condition, or disorder. Treating includes the administration of an compositions of present invention to prevent the onset of the symptoms or complications, alleviating the symptoms or complications, or eliminating the disease, condition, or disorder. Treating also encompasses therapeutic and palliative treatment. The aim of treatment includes the alleviation or prevention of symptoms, slowing or stopping the progression or worsening of a disease, disorder, or condition and/or the remission of the disease, disorder or condition. In certain embodiments, the treatment comprises anti-cancer therapy and/or treatments. The term "treatment" can be characterized by at least one of the following: (a) the reducing, slowing or inhibiting the growth of cancer and cancer cells, including slowing or inhibiting the growth of metastatic cancer cells; (b) preventing the further growth of tumors; (c) reducing or preventing the metastasis of cancer cells within a subject; (d) reducing or ameliorating at least one symptom of cancer. In some embodiments, the optimum effective amount can be readily determined by one skilled in the art using routine experimentation.

The term "effective amount" or "therapeutically effective amount" refers to an amount sufficient to effect beneficial or desirable biological and/or clinical results. That result can be reducing, inhibiting or preventing the growth of cancer cells, reducing, inhibiting or preventing metastasis of the cancer cells or invasiveness of the cancer cells or metastasis, or reducing, alleviating, inhibiting or preventing at least one symptoms of the cancer or metastasis thereof, or any other desired alteration of a biological system. An "effective treatment" refers to treatment producing a beneficial effect, e.g., amelioration of at least one symptom of a cancer. A beneficial effect can take the form of an improvement over baseline, i.e., an improvement over a measurement or observation made prior to initiation of therapy according to the method. A beneficial effect can also take the form of reducing, inhibiting or preventing further growth of cancer cells, reducing, inhibiting or preventing metastasis of the cancer cells or invasiveness of the cancer cells or metastasis or reducing, alleviating, inhibiting or preventing at least one symptoms of the cancer or metastasis thereof. Such effective treatment may, e.g., reduce patient pain, reduce the size or number of cancer cells, may reduce or prevent metastasis of a cancer cell, or may slow cancer or metastatic cell growth.

In one embodiment, the disclosure provides a method of treating cancer in a subject in need thereof comprising administering to the subject a therapeutically effective amount of the synergistic composition described herein.

In one embodiment, the method of treating cancer in a subject comprises administering to the subject a therapeutically effective amount of at least one cytotoxic ribonuclease and a therapeutically effective amount of at least one MAPK-pathway inhibitor which, when administered in combination, provide a synergistic effect to treat cancer.

In some embodiments, at least one MAPK-pathway inhibitor and at least one cytotoxic ribonuclease are administered concurrently or sequentially.

At least one cytotoxic ribonuclease and at least one MAPK-pathway inhibitor may be administered simultaneously/concurrently or sequentially. Simultaneous administration includes the administration of at least one cytotoxic ribonuclease and at least one MAPK-pathway inhibitor in two different formulations, taken separately but within an hour of administration of the first compound (e.g., seconds or minutes in-between). Suitably, when administered sequentially, for example, at least one cytotoxic ribonuclease may be administered first followed by administration of the MAPK-pathway inhibitor, or the MAPK-pathway inhibitor may be administered first followed by administration of at least one cytotoxic ribonuclease. The time between the administration of at least one cytotoxic ribonuclease and at least one MAPK-pathway inhibitor can be adjusted for maximum efficacy, and may be in the order of minutes, hours, days, or weeks.

At least one cytotoxic ribonuclease and at least one MAPK-pathway inhibitor may preferably be administered each with a pharmaceutically acceptable carrier selected on the basis of the selected route of administration and standard pharmaceutical practice for each component. The active agent may be formulated into dosage forms according to standard practices in the field of pharmaceutical preparations. See: Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, injectable solutions, troches, suppositories, or suspensions. For antibodies, suitable dosages forms are normally solutions.

For oral administration, the active ingredient may be combined with at least one solid inactive ingredient for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents. or lubricating agents.

For parenteral administration, the active agent may be mixed with a suitable carrier or diluent such as water, an oil (e.g., a vegetable oil), ethanol, saline solution (e, g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension, or emulsion.

The pharmaceutical composition is preferably in unit dosage form. In such form, the preparation is divided into unit doses containing appropriate quantities of the active component.

In some embodiments, the cytotoxic ribonuclease and the MAPK-pathway inhibitor are respectively contained in separate compositions; these may be of the same dosage form or of different dosage forms. For example, the two may be mutually different dosage forms, each of which is one among oral formulation, parenteral formulation, injectable formulation, drip formulation, and intravenous drip formulation; or the two may be the same dosage form.

Suitable dosages of the cytotoxic ribonuclease and the MAPK-pathway inhibitor can be determined by one skilled in the art. In one embodiment, the dose of the cytotoxic ribonuclease (e.g., ptRNase) and the MAPK-pathway inhibitor is calculated per mg/kg body weight. In another embodiment, the dose of the cytotoxic ribonuclease and the MAPK-pathway inhibitor is a fixed dose.

It will be appreciated that appropriate dosages of the cytotoxic ribonuclease and the MAPK-pathway inhibitor, and compositions comprising a cytotoxic ribonuclease and the MAPK-pathway inhibitor, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, or materials used in combination, and the age, sex, weight, condition, general health, and prior medical history of the patient. The amount of compound and route of administration will ultimately be at the discretion of the physician. Administration in vivo can be effected in one dose, continuously or intermittently (e.g., in divided doses at appropriate intervals) throughout the course of treatment.

Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

For example, in one embodiment, the recommended dose of dabrafenib is 150 mg orally twice daily, with trametinib at 2 mg orally once daily.

In some embodiments of the method of treatment, administration of the combination of at least one MAPK-pathway inhibitor and at least one cytotoxic ribonuclease results in synergistic inhibition of cancer growth.

In a further embodiment, the present disclosure provides a method of reducing or inhibiting cancer cell growth in a subject having cancer, the method comprising administering an effective amount of the synergistic composition comprising at least one MAPK-pathway inhibitor and at least one cytotoxic ribonuclease, wherein cancer cell growth is reduced or inhibited in the subject. The administration of the combination results in synergistic inhibition of cancer cell growth.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient suffering from, or at risk of developing, chemo-residual tumor cell growth.

In some embodiments, kits for carrying out the methods described herein are provided. The kits provided may contain the necessary components with which to carry out one or more of the above-noted methods. In one embodiment, a kit for treating cancer is provided. The kit may comprise at least one cytotoxic ribonuclease and at least one MAPK-pathway inhibitor and instructions for use in a synergistic combination. In some embodiments, the kit comprises at least one cytotoxic ribonuclease (e.g., ptRNase) and two or more MAPK-pathway inhibitors.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

The Examples below use a variant of human ptRNase (RNase 1) having diminished affinity for RI. Specifically, a ptRNase comprising the human RNase 1 (SEQ ID NO:1) with mutations at R4C/G38R/R39 G/N67R/G89R/S90R/V118C was used as an exemplary ptRNase, however other ptRNAases with diminished affinity for RI are contemplated to have similar synergistic effects against cancer cells, for example the ptRNases listed in paragraph [0036] above.

Example 1: Phosphorylation of Ribonuclease Inhibitor Modulates the Cytotoxicity of a Clinical Ribonuclease and the Synergistic Use of a Cytotoxic Ribonuclease in Combination with a MAPK Inhibitor In this Example, the inventors demonstrate the isolation and characterization of RI produced in a human cell. Human cells were found to append phosphoryl groups to five serine/threonine residues of RI. The nascent phosphoryl groups increase the already extraordinary affinity of RI for ptRNases, suggesting that even femtomolar affinity is not enough. The phosphorylation of RI is shown to arise from kinases in the ERK pathway. Well-known drugs that inhibit kinases in this pathway prevent RI phosphorylation, and their toxicity for tumor cells is increased markedly in the presence of an RI-evasive ptRNase. These findings reveal a link between seemingly unrelated cellular processes, and could lead to beneficial manifestations in the clinic.

This Example demonstrates the synergistic use of a cytotoxic ribonuclease in combination with a MAPK inhibitor against cancer cells.

The Data Demonstrate that Phosphorylation of RI Enhances its Interaction with ptRNases.

Figures 8A, 8B, 8C, 8D, 8E:
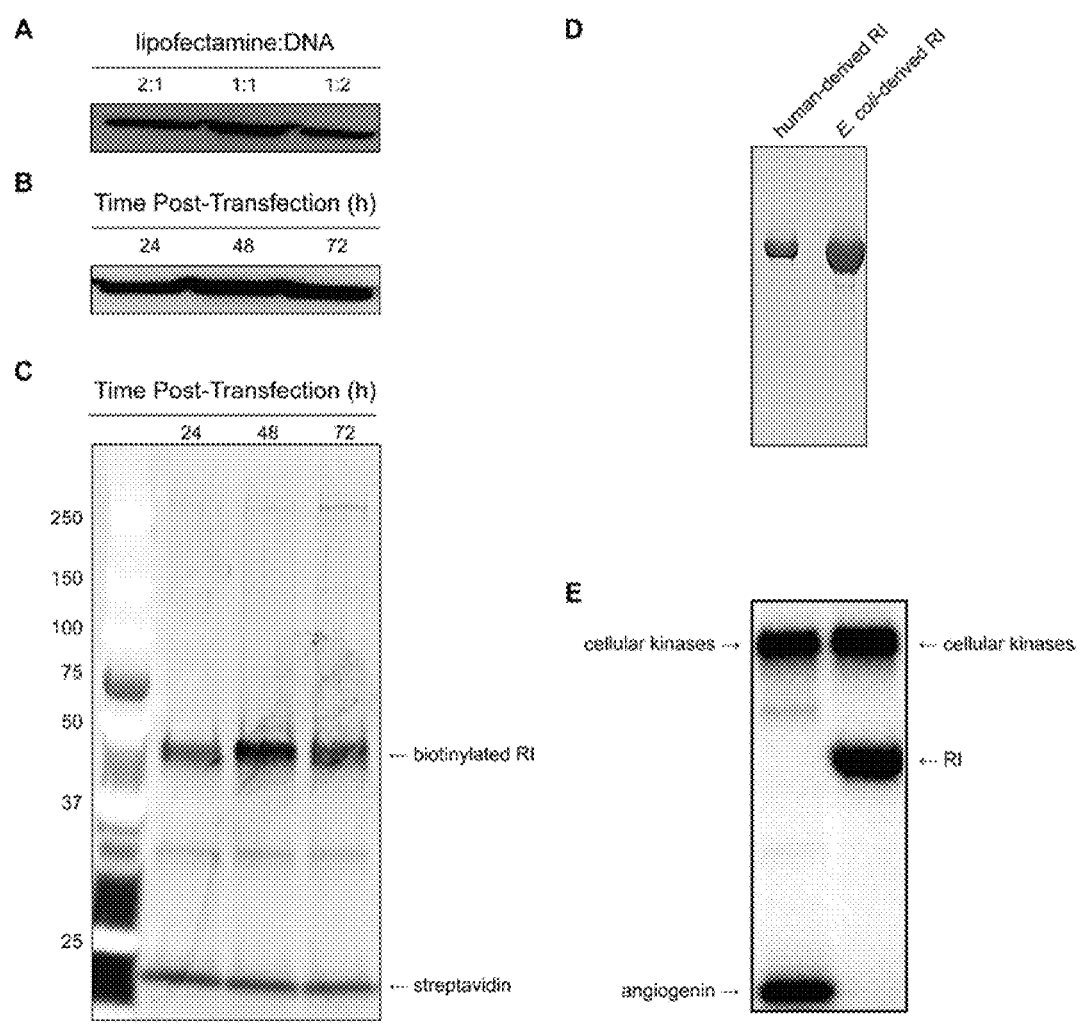
FIGS. 8A-8E show the expression and purification of biotinylated RI. Biotinylated RI was produced in HEK293T cells. Plasmids that direct the expression of BAP-RI and BirA were transfected transiently into cells. (A) Immunoblot showing that a 1:1 ratio of LIPOFECTAMINE® 3000 (a transfection reagent for nucleic acid delivery) to DNA plasmids yielded more biotinylated RI than did a 1:2 or 2:1 ratio. (B) Immunoblot showing that RI production was greater after transfection for 48 h than for 24 h or 72 h. (C) SD S-PAGE gel showing that RI production was greater after transfection for 48 h than for 24 h or 72 h. (D) SDS-PAGE gel showing human-derived RI (which is biotinylated) purified by chromatography using monomeric avidin agarose and an RNase A-affinity column. Elution of human-derived RI from an RNase A-affinity column required 3.5 M NaCl, whereas elution of E. coli-derived RI required 3.0 M NaCl. (E) Autoradiogram of a polyacrylamide gel showing that E. coli-derived RI is phosphorylated upon incubation with a HEK293T cell lysate and [$\gamma$-$^{32}$P] ATP.Human angiogenin (ANG), which is known to be phosphorylated (Hoang and Raines, 2017), serves as a positive control.

Biotinylated RI was produced in HEK293T cells through transient co-transfection of a plasmid that directs the expression of RI conjugated to a biotin-acceptor-peptide (BAP) and another plasmid that directs the expression of biotin ligase (BirA), which catalyzes the condensation of biotin with a lysine residue in BAP. Assays of different ratios of LIPOFECTAMINE® 3000 (a transfection reagent for nucleic acid delivery) to plasmids revealed a 1:1 ratio as yielding the most biotinylated RI (FIG. 8A). RI expression was found to be higher at 48 h after transfection than at 24 or 72 h (FIGS. 8B and 8C). Biotinylated RI was purified by column chromatography using monomeric avidin-agarose and RNase A-affinity resin. Elution of biotinylated RI from the RNase A-affinity resin required 3.5 M NaCl, in contrast to the 3.0 M NaCl necessary to elute RI produced in *Escherichia coli* (FIG. 8D). Elution at a higher salt concentration suggests a greater affinity of a ptRNase for mammalian-derived RI.

We hypothesized that mammalian-derived RI undergoes phosphorylation. Coulombic interactions make a strong contribution to the affinity of RI and ptRNases, which are highly anionic and highly cationic, respectively. The addition of anionic phosphoryl groups to RI would likely enhance this Coulombic interaction.

Figures 1A, 1B, 1C, 1D, 1E:
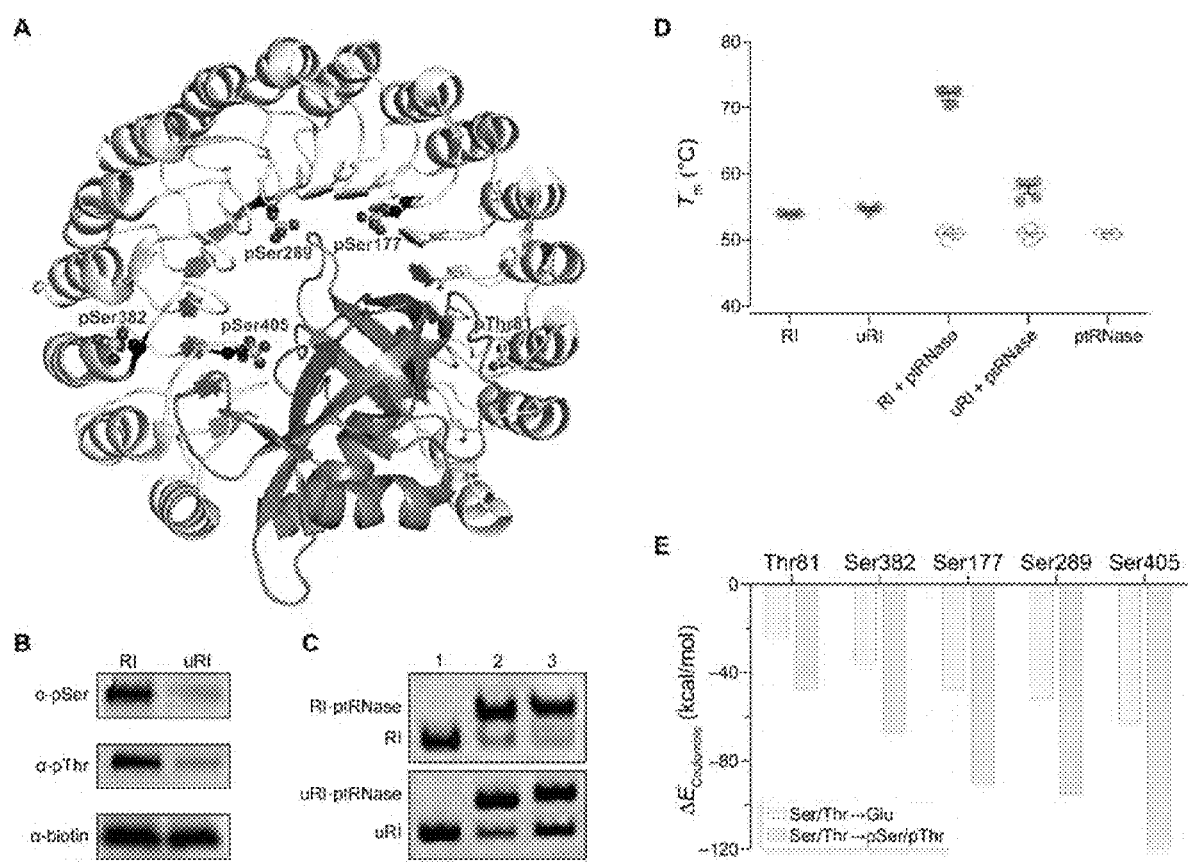
FIGS. 1A-1E demonstrate the characterization of phosphorylated RI. (A) Structure of the RI•RNase 1 complex (PDB entry 1z7x). Phosphorylated residues identified by mass spectrometry are modeled and depicted in ball-and-stick representation. Image was created with the program PyMOL from Schrödinger (New York, N.Y.). (B) Immunoblots showing that RI produced by HEK293T cells is recognized by an anti-phosphoserine antibody ($\alpha$-pSer) and anti-phosphothreonine antibody ($\alpha$-pThr). That recognition is eliminated upon treatment with lambda protein phosphatase (unphosphorylated RI, uRI). (C) Non-denaturing PAGE gel showing complex formation of RI and the ptRNase. Lane 1, free RI (3.0 µM); lanes 2 and 3, complex of RI (3.0 µM) with the ptRNase (4.0 µM and 3.0 µM). Proteins (in PBS) were incubated for 20 min prior to loading on the gel. (D) Graph showing that RI and uRI have similar thermostability. The presence of the ptRNase increases the $T_m$ value of RI by 18° C. In contrast, the presence of the ptRNase increases the $T_m$ value of uRI by only 3° C. Individual circles represent the mean±SEM (n 3, technical replicates). (E) Graph showing energies calculated for changes in Coulombic interaction between RI and RNase 1 upon phosphorylation of RI at particular Ser/Thr residues.
Figure 9:
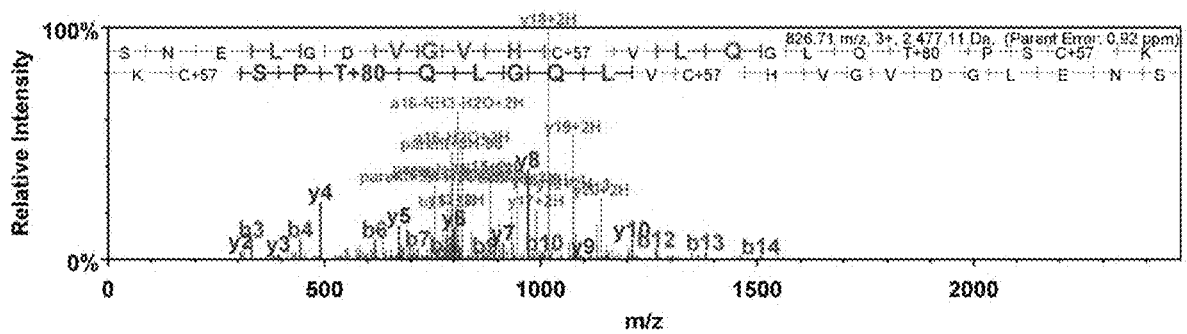
FIG. 9 shows the MS/MS mass spectra of tryptic peptides from RI that were used to identify phosphorylation sites. Motinylated RI was produced in HEK293T cells and purified with RNase A-affinity chromatography. Purified RI was digested with trypsin, and the ensuing peptides were analyzed to identify phosphorylation sites. Five sites were identified: Thr81, Ser177, Ser289, Ser382, and Ser405 from at least 2 biological replicates.
Figure 9:
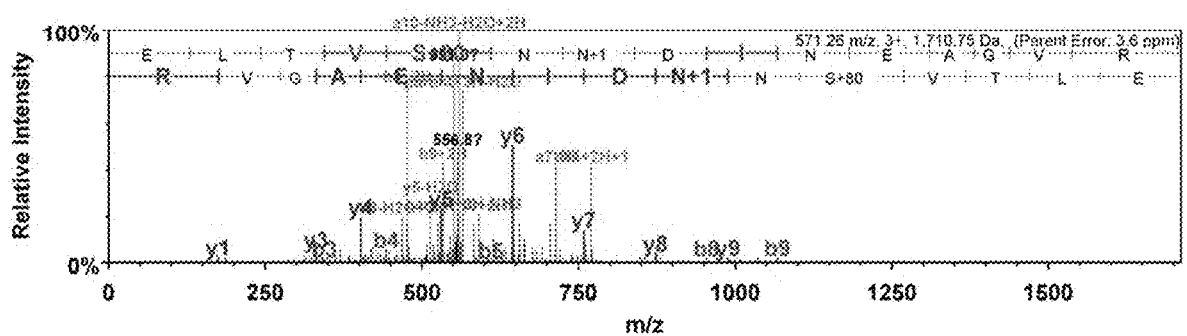
Figure 9:
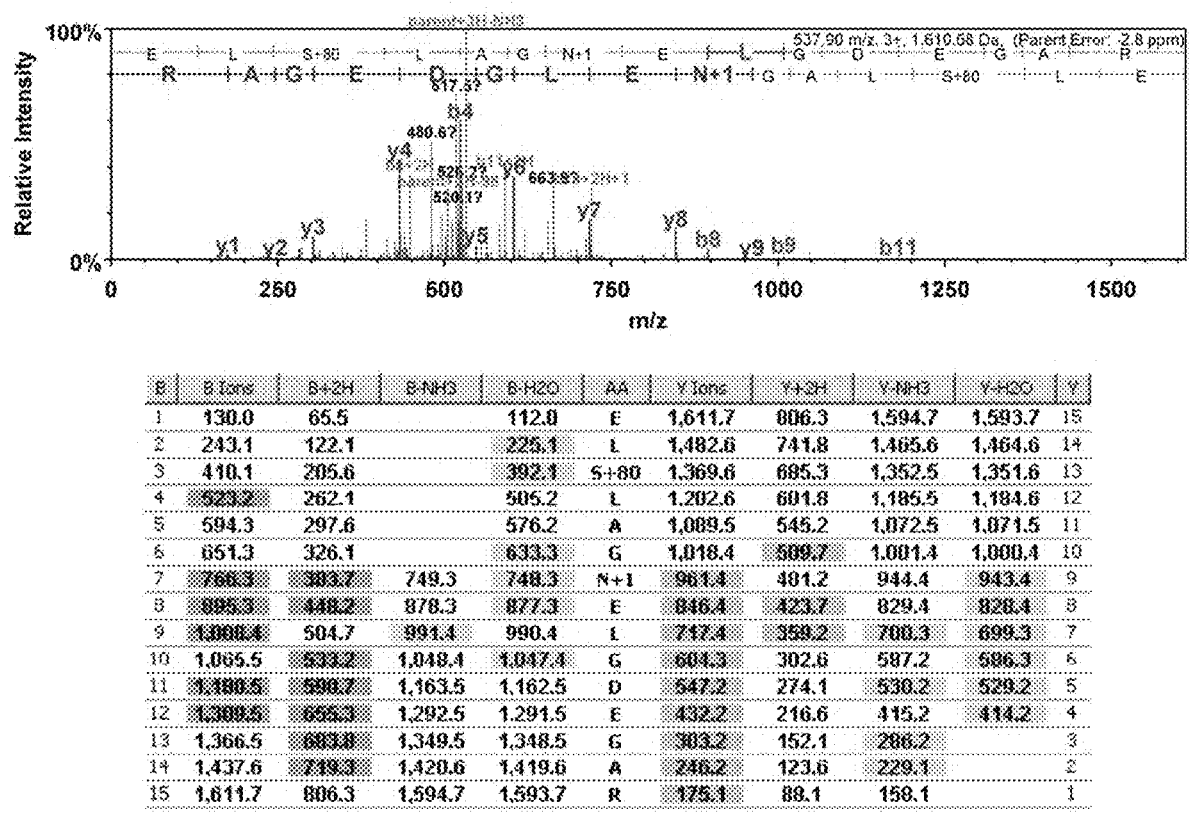
Figure 9:
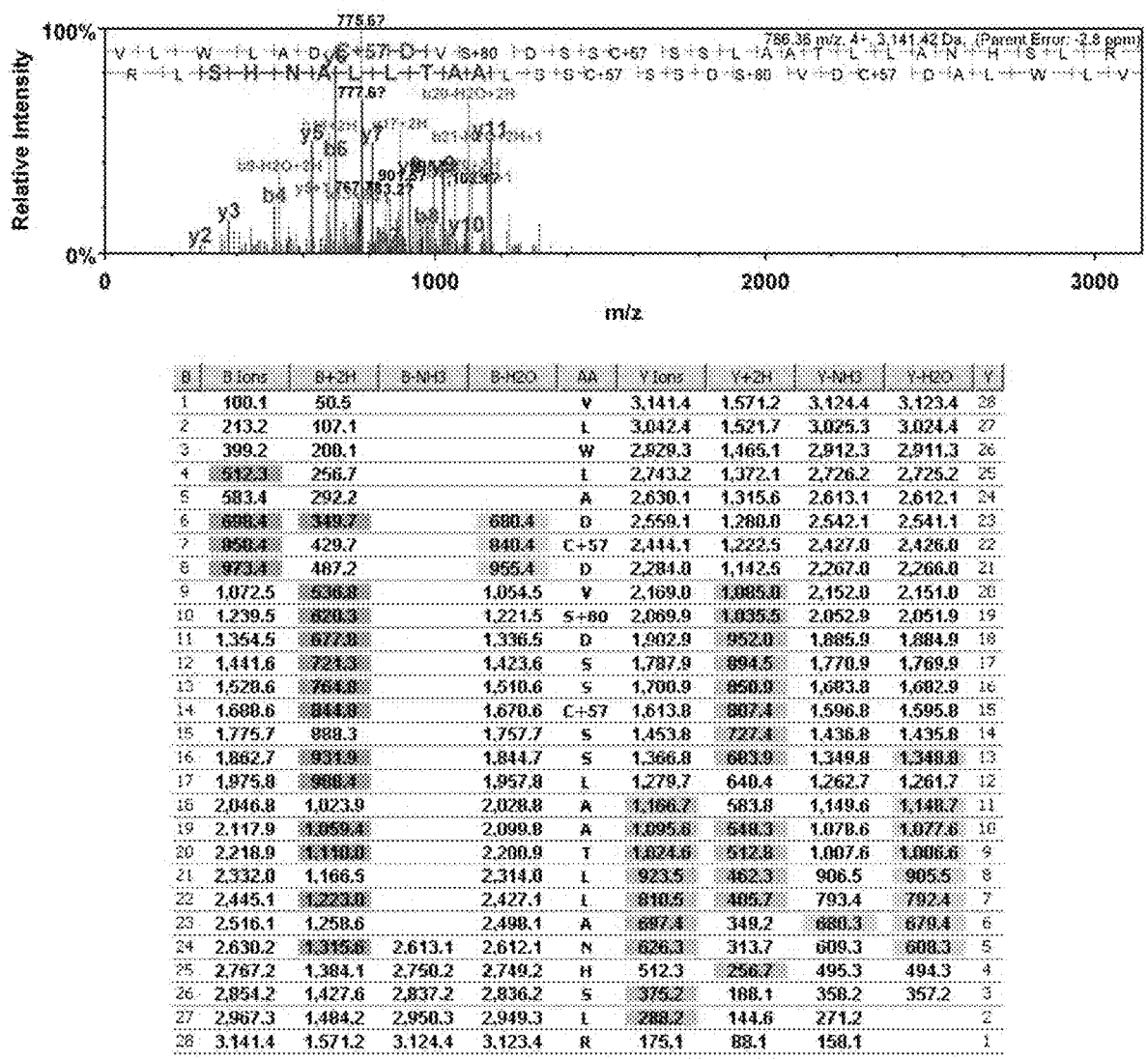
Figure 9:
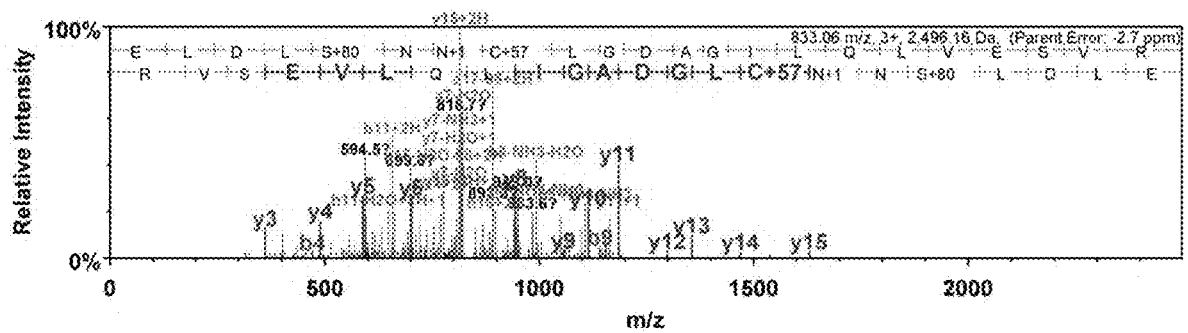

We discovered that RI is indeed phosphorylated by intracellular kinases. Incubation of *E. coli*-derived RI with HEK293T cell lysate and [$\gamma$-$^{32}$P]ATP led to $^{32}$P-labeled RI (FIG. 8E). Five phosphorylation sites were identified on the human-derived RI by mass spectrometry: Thr81, Ser177, Ser289, Ser382, and Ser405 (FIG. 9). The phosphorylation of RI was validated further by immunoblotting with antibodies that recognize phosphoserine ($\alpha$-pSer) and phosphothreonine ($\alpha$-pThr) (FIGS. 1A and 1B). Application of lambda protein phosphatase to the same sample produced unphosphorylated (uRI), which did not yield a signal in the immunoblot.

We interrogated the effect of RI phosphorylation using a native gel-shift assay. In these assays, we used a variant of human ptRNase (RNase 1) having diminished affinity for RI. The ptRNases with diminished affinity for RI are directed towards cancer cells by an innate affinity for Globo H, which is a tumor-associated antigen (Eller, 2015), and this ptRNase has been in a clinical trial as a cancer chemotherapeutic agent (Strong et al., 2012b; Strong et al., 2012a). An equimolar or greater amount of the ptRNase was incubated with RI, and a shift in the position of RI on the gel reported on the extent of complex formation. Although phosphorylated RI exhibits near-complete binding to the ptRNase upon incubation, uRI splits into free and ptRNase-bound populations, indicative of incomplete binding (FIG. 1C). Thus, the presence of phosphoryl groups on RI enhances its interaction with ptRNases.

The enhanced affinity of phosphorylated RI for a ptRNase was also apparent in thermal denaturation experiments. While not changing the thermostability of RI itself, phosphorylation generates a marked increase in the thermostability of an RI•ptRNase complex (FIG. 1D). The $T_m$ value of the phosphorylated RI•ptRNase complex is 15° C. higher than that of RI•ptRNase, indicative of enhanced affinity and in accord with the results of the native gel-shift assay (FIG. 1C). Moreover, computational models suggest a stronger Coulombic interaction between RI and RNase 1 upon phosphorylation of RI, especially on residues closest to the RI-RNase 1 interface (FIG. 1E). Together, these data indicate a direct link between the phosphorylation of RI and an increase in its affinity for ptRNases.

The Results Show that RI is a Substrate for Kinases of the ERK Pathway.

We sought to identify the kinases that phosphorylate RI. For guidance, we analyzed the amino-acid sequence of RI with the program NetPhos 3.1 (Blom et al., 1999; Blom et al., 2004). The computational results indicated that RI was likely to be a substrate for ERK and RSK. We then treated cells with trametinib, which is an FDA-approved small-molecule inhibitor of MEK—an upstream activator of the ERK-RSK pathway (Yamaguchi et al., 2011; Lugowska et al., 2015). To evaluate the consequences of phosphorylation in cellulo, we used a cell viability assay. We reasoned that inhibiting the phosphorylation of RI would liberate more unbound ptRNase, enabling this ptRNase to manifest its cytotoxicity more strongly.

Figure 2:
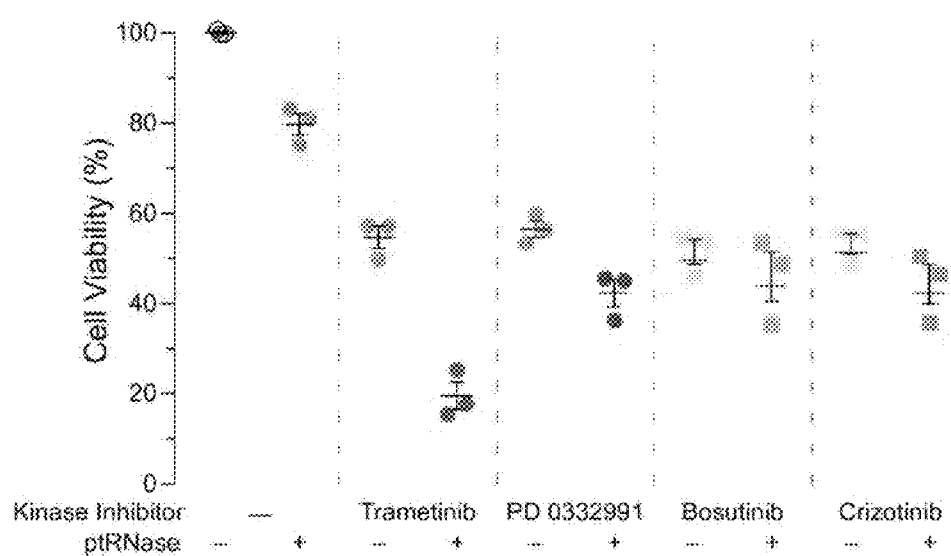
FIG. 2 is a graph demonstrating an ERK-pathway inhibitor enhances the toxicity of a ribonuclease toward human lung cancer cells. A549 cells were treated with kinase inhibitors at their $EC_{50}$ concentrations (Table 1) for 1 h prior to the addition of the ptRNase (10 µM) or vehicle. Cell viability was assessed after another 48 h. Treatment with trametinib combined with the ptRNase is highly effective at killing lung cancer cells. Combinations of the ptRNase with other kinase inhibitors result in toxicity similar to that from the kinase inhibitor alone. Values represent the mean±SEM (n=3, biological replicates).

To test this hypothesis, we treated human lung cancer cells for 48 h with trametinib or with three other kinase inhibitors: PD 0332991 (which is a CDK4/CDK6 inhibitor), bosutinib (which is a Src family kinase inhibitor), or crizotinib (which is an ALK inhibitor) (Boschelli et al., 2001; Fry et al., 2004; Zou et al., 2007). We measured cell viability with a tetrazolium dye-based assay for metabolic activity. The ensuing $EC_{50}$ values are listed in a Table 1 and in the table in FIG. 10. Next, we treated cells with kinase inhibitors at their $EC_{50}$ concentrations for 1 h prior to the addition of the ptRNase (10 μM), and assessed cell viability after 48 h. We found that treatment with trametinib in combination with the ptRNase was more effective at killing lung cancer cells than was treatment with either agent by itself (FIG. 2). Combinations of the ptRNase with other kinase inhibitors result in cytotoxicity comparable to treatment with kinase inhibitor alone. These data are consistent with RI being a substrate for kinases of the ERK pathway.

TABLE 1

Toxicity of agents for human lung cancer cells (A549)

| Agent | Kinase Target | $EC_{50}$ (μM)* | Synergism with ptRNase? |
|---|---|---|---|
| Kinase Inhibitor (non-ERK pathway) | | | |
| PD 0332991 | Cdk4 and Cdk5 | 0.24 ± 0.04 | No |
| Bosutinib | c-Src and Abl | 0.73 ± 0.06 | No |
| Crizotinib | c-MET and ALK | 0.11 ± 0.02 | No |
| Kinase Inhibitor (ERK pathway) | | | |
| Trametinib | MEK1/2 | 5.7 ± 0.6 | Yes |
| Selumetinib | MEK1/2 | 43 ± 5 | Yes |
| ARS-853 | (KRAS$^{G12C}$) | 74 ± 8 | Yes |
| Dabrafenib | BRAF$^{V600E}$ | 40 ± 5 | Yes |
| ptRNase | | | |
| ptRNase | (RNA) | 62 ± 7 | — |

*Values (±SE) are for cell viability as measured with a tetrazolium dye-based assay for metabolic activity (n = 3, biological replicates).

Data Demonstrate MEK Inhibitors Act Synergistically with a ptRNase

Figure 3A:
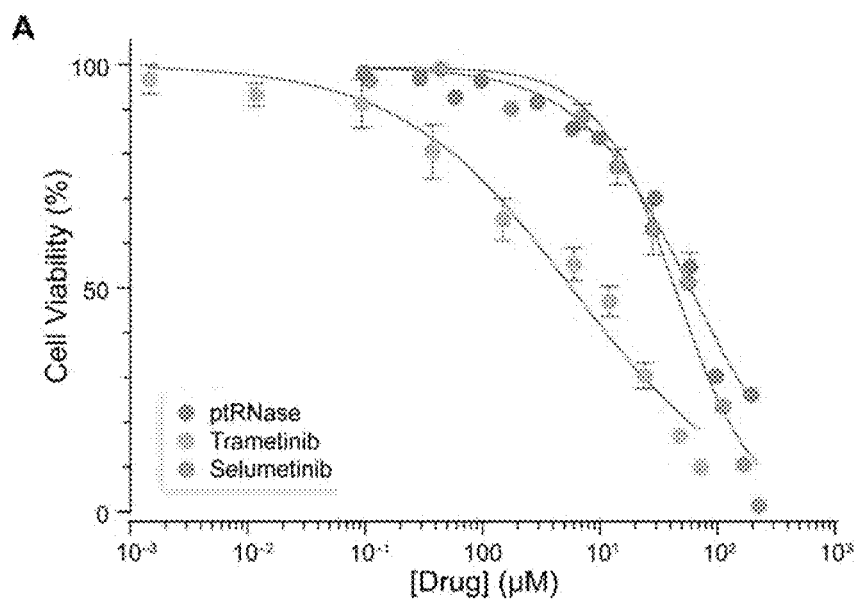
FIGS. 3A-3C depict synergistic effects of ERK-pathway inhibitors and the ptRNase on the viability of human A549 lung cancer cells. (A) Cells were incubated with a single drug (trametinib, selumetinib, or the ptRNase) for 48 h. Cell viability was measured with a tetrazolium dye-based assay for metabolic activity. EC50 values are listed in Table 1. (B, C) Two-drug combination experiments were performed using a 5×5 matrix to interrogate 25 concentration pairs. Cells were treated with a kinase inhibitor for 1 h at 37° C., followed by the addition of the ptRNase. Cells were incubated continually for another 48 h. Cell viability assessments for single and combination drug treatments were evaluated to identify synergistic effects based on CI. Values of CI were calculated with CalcSyn 2.0 software. CI<1 (blue), CI=1, and CI>1 (dark grey) indicate synergism, an additive effect, and antagonism respectively. The two-drug combination of trametinib and the ptRNase exerts more synergism than does the combination of selumetinib and the ptRNase. Values represent the mean±SEM (n=3, biological replicates).
Figure 3B:
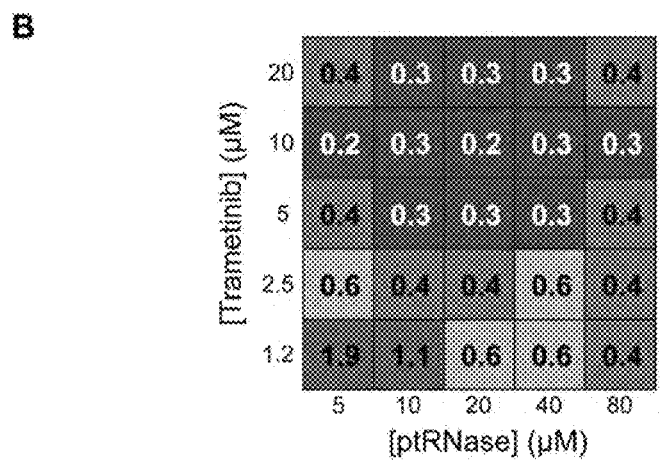
Figure 3C:
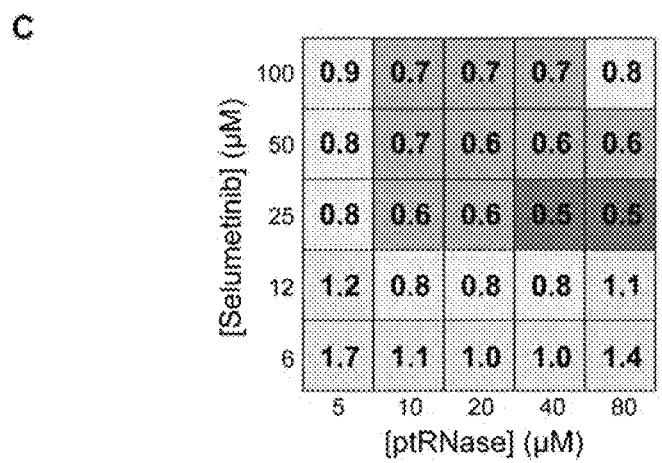

We then set out to evaluate combinations of kinase inhibitors and the ptRNase. First, we characterized the cytotoxicity of single-drug treatments in human A549 lung cancer cell line (FIG. 3A). We used the $EC_{50}$ values obtained from single-drug treatment (Table 1) to design subsequent drug combination experiments. Two-drug combination experiments were performed using a 5×5 matrix to interrogate 25 concentration ratios per combination. A MEK inhibitor (trametinib or selumetinib) and the ptRNase were assessed at five concentrations obtained by serial two-fold dilutions. We assessed cell viability for single-drug and two-drug combination treatments to identify synergistic effects as judged by values of the combination index (CI), which are shown in FIGS. 3B and 3C. We observed strong synergy between MEK inhibitors and the ptRNase, and the synergistic effect of the ptRNase paired with trametinib is more favorable than with selumetinib.

Data Demonstrate KRAS Inhibitors Act Synergistically with a ptRNase.

A BRAF inhibitor was also shown to act synergistically with the ptRNase. MEK is activated by BRAF, and BRAF is a substrate of KRAS. We asked if an inhibitor of the upstream activator, KRAS, acts synergistically with the ptRNase. ARS-853 dabrafenib (trade name Tafinlar, GSK2118436), sorafenib (BAY43-9006, Nexavar), vemurafenib (PLX4032), PLX 4720, GDC-0879, and LGX818 have robust cellular inhibitory activity against the G12C variant of KRAS (Patricelli et al., 2016; Lito et al., 2016) and inhibit KRAS signaling in H358 cells ($KRAS^{G12C}$) but not A549 cells ($KRAS^{G12S}$) (Patricelli et al., 2016), which are human lung cancer lines. As expected, ARS-853 treatment killed H358 cells more effectively than A549 cells (FIGS. 4A and 4B). Interestingly, ptRNase treatment was 20-fold more cytotoxic to H358 cells compared to A549 cells (FIGS. 4A and 4B). Combining the $KRAS^{G12C}$-targeted agent, ARS-853, with the ptRNase enhanced the efficacy of both agents towards H358 cells (FIG. 4C). In contrast, this combination produced an additive effect towards A549 cells (FIG. 4D). These findings are again consistent with a mechanism in which inhibition of the ERK pathway prevents RI phosphorylation, making cancer cells more vulnerable to the ptRNase.

The Data Show that the ptRNase Exhibits Greater Synergy with a BRAF or MEK Inhibitor than do Combinations of BRAF and MEK Inhibitors.

Substitutions to Val600 of BRAF lead to strongly growth-promoting signals and are often found in patients with advanced melanoma. Trametinib, in combination with dabrafenib, is in clinical use for the treatment of patients with $BRAF^{V600E/K}$ metastatic melanoma. Dabrafenib has robust inhibitory activity against the V600E/K variants of BRAF (Kefford et al., 2010; King et al., 2013). Tumors often develop resistance to BRAF inhibitors by activating the MEK pathway and resuming growth (Greger et al., 2012; Long et al., 2015; Kong et al., 2017; Long et al., 2017).

Figures 10A, 10B, 10C, 10D:
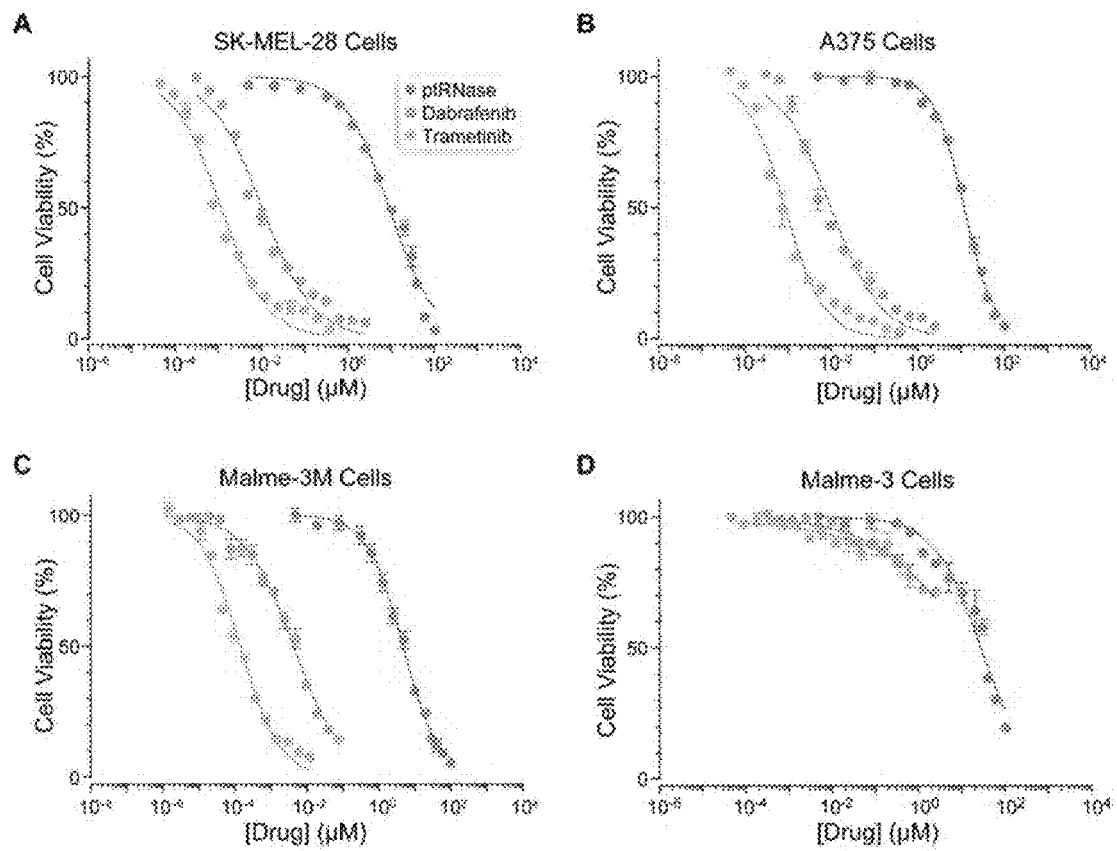
FIGS. 10A-10D show the effect of kinase inhibitors and the ptRNase on the viability of human melanoma cells. Cell viability was measured with a tetrazolium dye-based assay for metabolic activity. $EC_{50}$ values are listed in the table.

We assessed the effect of kinase inhibitors in combination with the ptRNase across three melanoma cell lines: SK-MEL-38, A375, and Malme-3M. We observed strong synergy with dabrafenib and the ptRNase, and somewhat weaker synergy with trametinib and the ptRNase; whereas dabrafenib and trametinib exhibited an additive effect (FIG. 5). None of the agents were toxic to normal skin fibroblasts at the tested doses (FIG. 10).

The Data Show Phosphorylation of RI is Suppressed by Inhibitors of the ERK Pathway.

Figures 6A, 6B:
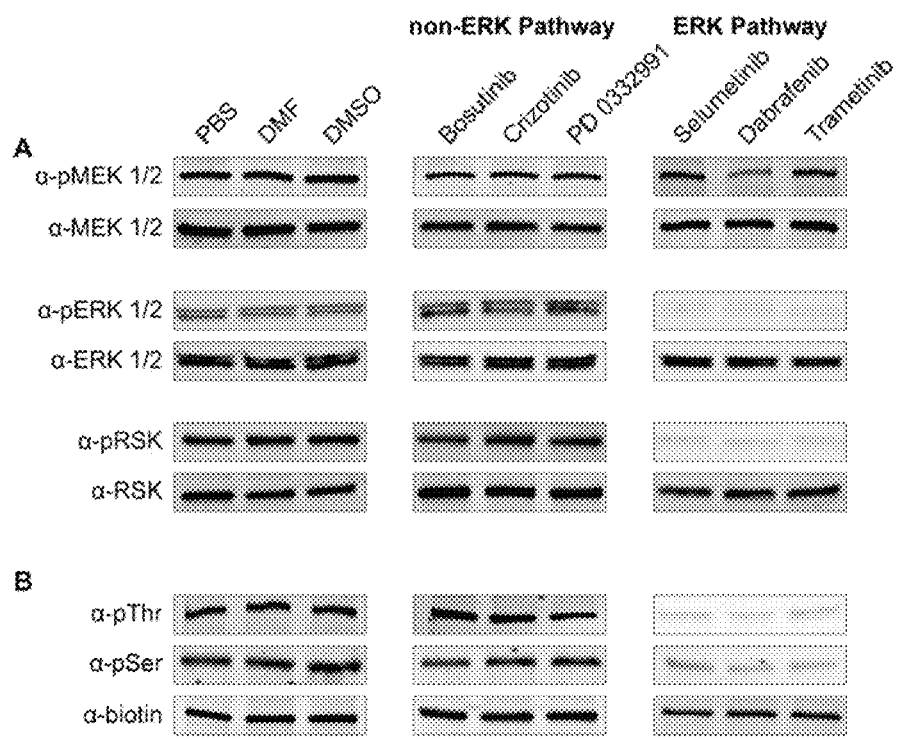
FIGS. 6A-6B are immunoblots showing that inhibition of the ERK pathway prevents the phosphorylation of RI in SK-MEL-28 cells. Cells transfected to produce biotinylated RI were treated with bosutinib (5 µM), crizotinib (2 µM), PD 0332991 (2 µM), selumetinib (10 nM), dabrafenib (10 nM), or trametinib (1 nM) for 24 h. (A) Treatment with inhibitors of non-ERK pathway kinases has no effect on the phosphorylation of MEK, ERK, or RSK in cell lysates. Treatment with dabrafenib reduces the phosphorylation of MEK ($\alpha$-pMEK 1/2 lane) as well as that of ERK and RSK ($\alpha$-pERK 1/2, and $\alpha$-pRSK lanes). Treatment with selumetinib and trametinib reduces the phosphorylation of ERK and RSK. (B) Treatment with inhibitors of non-ERK pathway kinases has no effect on phosphorylation of biotinylated RI, which was captured by using streptavidin-coated magnetic beads. Inhibition of ERK-pathway kinases diminishes phosphorylation of RI ($\alpha$-pThr, and $\alpha$-pSer lanes).

The inventors further confirmed the apparent effect of kinase inhibitors on RI phosphorylation by immunoblotting. Biotinylated RI was isolated by using streptavidin-coated magnetic beads from SK-MEL-28 cells after transient transfection for 48 h. To detect phosphorylated species, we used α-pSer or α-pThr. Strong bands for phosphorylated RI were observed when cells were treated with inhibitors of kinases that are not on the ERK pathway (FIG. 6). Those kinase inhibitors (PD 0332991, bosutinib, and crizotinib) had insignificant effects on the phosphorylation of MEK, ERK, or RSK (FIG. 6A). In contrast, cells treated with a BRAF-targeted agent, dabrafenib, produced only a weak band of phosphorylated MEK, and no detectable phosphorylation of downstream targets, including ERK, RSK, and RI. Likewise, treatment with MEK-targeted agents, trametinib or selumetinib, diminished the phosphorylation of ERK, RSK, and RI. These biochemical data provide direct evidence that kinases in the ERK pathway are indeed responsible for phosphorylating RI, in agreement with the observed synergism.

Below we discuss the meaning of our observations described in this Example. RI was discovered in the 1950s (Pirotte and Desreux, 1952; Roth, 1953; Roth, 1956). The imperative for its existence, however, became known only recently. The natural ligands of RI, ptRNases, are not only highly efficient catalysts of RNA degradation (Raines, 1998), but also enter cells spontaneously (Chao et al., 2010; Chao and Raines, 2011). Moreover, ptRNases circulate in human blood and serum at a concentration of ~0.5 µg/mL (Lomax et al., 2017). Accordingly, a potent cytosolic inhibitor, RI, has co-evolved with ptRNases (Haigis et al., 2002; Lomax et al., 2014). ptRNases that evade RI are cytotoxic (Rutkoski and Raines, 2008; Lomax et al., 2012).

The affinity of RI for ptRNases has been measured to be as high as 0.01 fM (Lomax et al., 2014). Apparently, that is not enough. We discovered that five residues of RI are phosphorylated by kinases in the ERK pathway (FIGS. 1A and 1B), and that phosphorylation increases the affinity of RI for a ptRNase (FIGS. 1C and 1D). Computational models suggest that three of the nascent phosphoryl groups (i.e., those on Ser177, Ser289, and Ser405) are especially favorable for interaction with bound RNase 1 (FIG. 1E). These three sites have been conserved during mammalian evolution (FIG. 11).

The phosphoryl group on Ser405 merits special consideration. ptRNases have four well-defined enzymic subsites that bind to phosphoryl groups in an RNA substrate (Fontecilla-Camps et al., 1994; Fisher et al., 1998). A phosphoryl group on Ser405 is proximal to each of those subsites in a RI•ptRNase complex (FIG. 12). In other words, a posttranslational modification installs a phosphoryl group in the inhibitor of an enzyme in a location that recapitulates the phosphoryl groups in the substrate of that enzyme.

RI inhibits an atypical ptRNase-ANG, which is a potent inducer of neovascularization (Fett et al., 1985). Whereas other ptRNases function in the extracellular space or cytosol, ANG acts in the nucleolus (Moroianu and Riordan, 1994; Xu et al., 2002). Gain- and loss-of-function experiments have elucidated the roles of RI in regulating angiogenesis through direct interaction with ANG (Shapiro and Vallee, 1987; Pizzo and D'Alessio, 2007; Dickson et al., 2009; Li et al., 2014; Lyons et al., 2017). Phosphorylation enables ANG to evade cytosolic RI on its route to the nucleolus (Hoang and Raines, 2017). Appending phosphoryl groups to RI generates repulsive Coulombic interactions that are likely to diminish its affinity for ANG even further. In particular, Ser289 of RI is proximal to phosphorylated Ser87 of ANG in the RI•ANG complex (FIG. 13A), and Ser405 of RI is close to Asp41 of ANG (FIG. 13B). Notably, Ser87 is not known to be phosphorylated in other ptRNases, and Asp41 is nearly always replaced with a proline residue in homologs (Beintema et al., 1988). Thus, phosphorylation might enable RI to discriminate between homologous human proteins-enhancing affinity for RNase 1 but diminishing affinity for ANG.

Figures 14A, 14B, 14C:
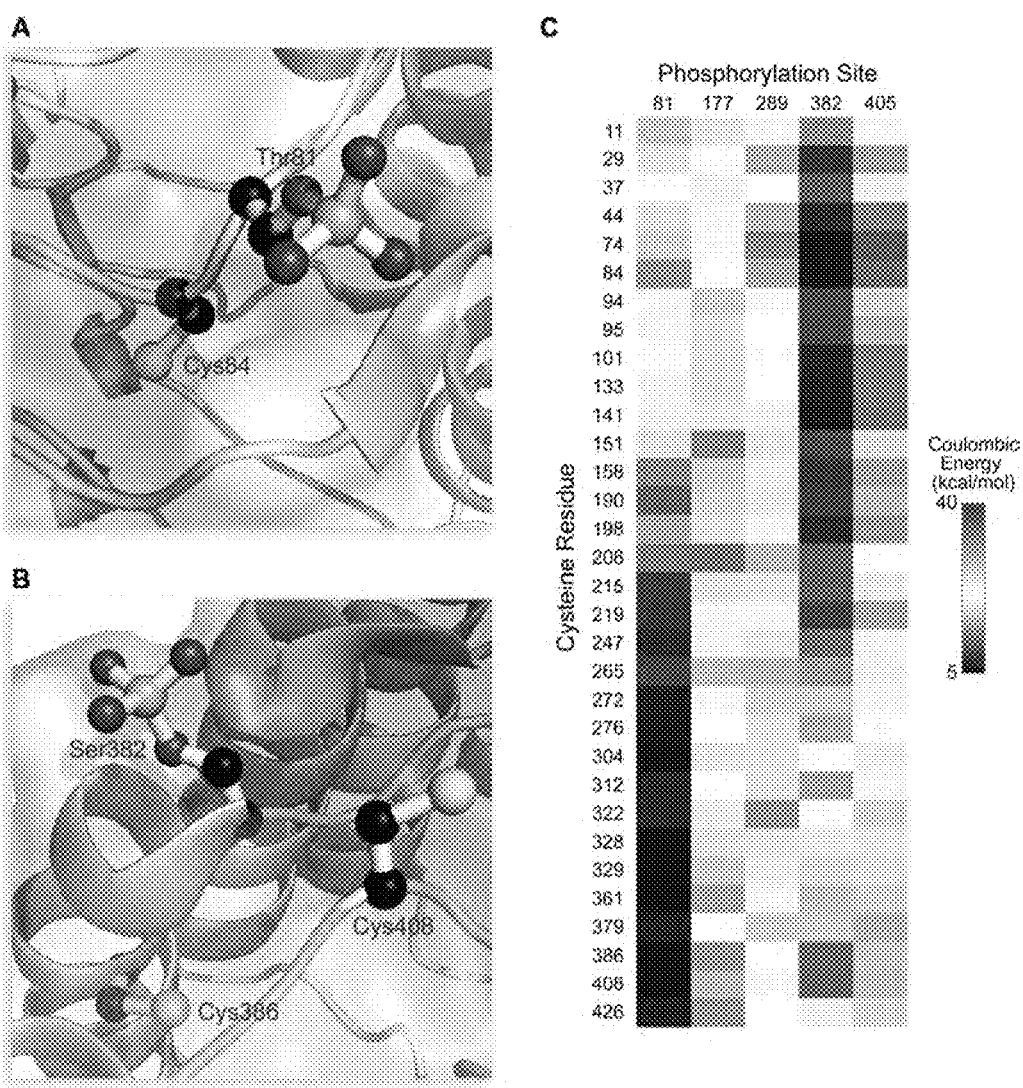
FIGS. 14A-14C demonstrate the effect of RI phosphorylation on its oxidative stability. (A, B) Images showing the proximity of a phosphoryl group on Thr81 or Ser382 to cysteine residues of RI. A phosphoryl group was installed computationally on $O^\gamma$ of Thr81 and Ser382. RI is depicted as a gray ribbon; ANG is depicted as a green ribbon. The image was made with PDB entry 1z7x and the program PyMOL. (C) Heat map of the change in Coulombic interaction energy between each cysteine thiolate on RI and the rest of the protein upon phosphorylation at Thr81, Ser177, Ser289, Ser382, or Ser405. In general, phosphorylation hinders thiolate formation at cysteine residues, especially those proximal to the phosphorylation site.
Figure 15:
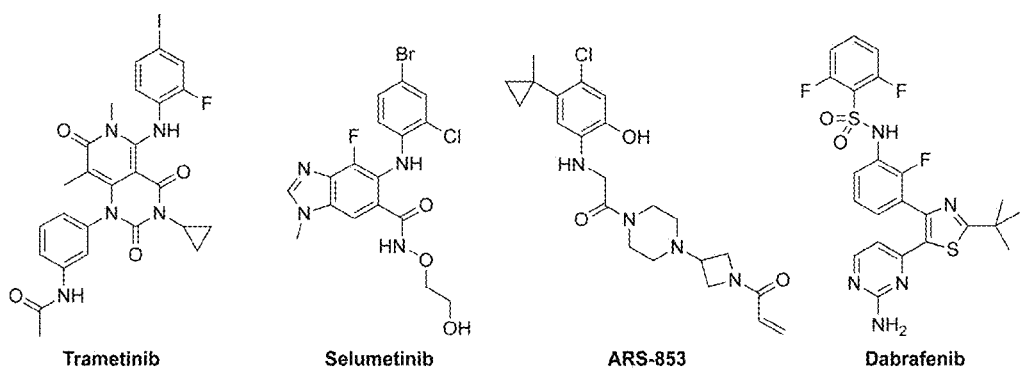
FIG. 15 provides the structures of exemplary inhibitors as used in Table 1.

Whereas the phosphorylation of Ser177, Ser289, and Ser405 of RI affects its affinity for ptRNases, the phosphorylation of Thr81 and Ser382 could affect the oxidative stability of RI. Both of these residues are proximal to cysteine residues in the folded protein (FIGS. 14A and 14B). RI is vulnerable to cooperative oxidation (Fominaya and Hofsteenge, 1992; Ferreras et al., 1995) that is detrimental to its structure and function, and leads to proteolysis (Lee and Vallee, 1993; Hofsteenge, 1997). A sulfhydryl group is oxidized much more readily upon deprotonation to a thiolate (Poole, 2015), which is anionic. Accordingly, cysteine residues in an anionic environment are likely to be resistant to oxidation (FIG. 14C), and the phosphorylation of RI could confer such resistance.

RI is phosphorylated by kinases of the ERK pathway. The ERK pathway is deregulated in a third of all human cancers (Dunn et al., 2005; Torii et al., 2006; Dhillon et al., 2007). Small-molecule inhibitors that target components of the ERK cascade can halt the propagation of growth stimuli and be effective anti-cancer agents (Knight and Shokat, 2005; Roberts and Der, 2007; Knight et al., 2010). The development of resistance, however, limits the effectiveness of these inhibitors (McCubrey et al., 2007). For example, trametinib and dabrafenib were approved in 2013 as single agents for the treatment of $BRAF^{V600E/K}$ mutation-positive unresectable or metastatic melanoma (King et al., 2013; Lugowska et al., 2015). Many patients, however, develop resistance to these drugs within a few months. In 2014, the FDA granted approval for a combination therapy of trametinb and dabrafenib, with the hope of combatting resistance (Long et al., 2015; Long et al., 2017). In 2017, this combination was approved for the treatment of metastatic non-small cell lung cancer with BRAF V600E mutation. We find that coupling either trametinib or dabrafenib with a cytotoxic ptRNase provides much more synergistic toxicity for melanoma cells than does coupling trametinib with dabrafenib (FIG. 5). This synergism between a kinase inhibitor and a ptRNase is consistent with underlying mechanisms of action (FIG. 7) as well as rational strategies for the beneficial combination of drugs (Dancey and Chen, 2006; Lopez and Banerji, 2016). Hence, the discovery of RI phosphorylation could have clinical implications, including to cancer patients suffering from "addiction" to drugs that target the ERK pathway (Kong et al., 2017).

Materials and Methods

Materials

All chemicals were from Sigma-Aldrich (St. Louis, Mo.), Invitrogen (Carlsbad, Calif.), or Thermo Fisher Scientific (Waltham, Mass.) unless indicated otherwise, and were used without further purification. All primary antibodies were from Cell Signaling Technology (Danvers, Mass.). All secondary antibodies were from Santa Cruz Biotechnologies (Santa Cruz, Calif.). The ptRNase was a kind gift from Dr. L. E. Strong (Quintessence Biosciences, Madison, Wis.). All kinase inhibitors were from Selleckchem (Houston, Tex.). Aqueous solutions were made with water that was generated with an Atrium Pro water purification system from Sartorius (Bohemia, N.Y.) and had resistivity ≥18 MΩ·cm$^{-1}$. Procedures were performed at room temperature (~22° C.) unless indicated otherwise.

Cell Culture

Human cells were from American Type Culture Collection (ATCC) (Manassas, Va.) and were maintained according to recommended procedures. Medium and added components, trypsin (0.25% w/v), and Dulbecco's phosphate-buffered saline (PBS) were from the GIBCO® brand from Thermo Fisher Scientific (Waltham, Mass.). Cells were grown in flat-bottomed culture flasks in a cell-culture incubator at 37° C. under $CO_2$(g) (5% v/v). A549 cells (ATCC CCL-185) were grown in F-12K medium; H358 (ATCC CRL-5807) cells were grown in RPMI-1640 medium; SK-MEL-28 cells (ATCC HTB-72) were grown in Eagle's minimum essential medium; A375 cells (ATCC CRL-1619) and 293T cells (HEK) were grown in Dulbecco's modified Eagle's medium; Malme-3M (HTB-64) cells were grown in Iscove's modified Dulbecco's medium; Malme-3 (HTB-102) cells were grown in McCoy's 5a modified medium. The Corning 96-well microplates used in experiments were from Sigma-Aldrich.

Cloning of BAP-RI and BirA

A DNA fragment encoding human wild-type RI was a generous gift from Promega (Fitchburg, Wis.). DNA primers encoding BAP and a linker peptide, GSGSGS, were installed on the N terminus of RI by amplification using PCR. The PCR-amplified gene encoding the BAP-RI conjugate was inserted into pNeo3 vector by using Gibson Assembly (Gibson et al., 2009). A DNA fragment encoding BirA was a kind gift from Prof. M. Wickens (University of Wisconsin-Madison). The gene was inserted into pNeo3 vector by using Gibson Assembly. The sequences of the BAP-RI and Bir A constructs were confirmed by DNA sequencing at the University of Wisconsin Biotechnology Center.

Expression and Purification of Biotinylated RI

HEK293T cells were seeded in complete medium in 6-well plates or 10-cm dishes at a density of 200 cells/4. After 24 h, cells were transfected with BirA and BAP-RI plasmids using LIPOFECTAMINE® 3000 (a transfection reagent for nucleic acid delivery) . One hour later, biotin (1 μM) was added into transfected cells, and incubation was continued for another 48 h. Cells were harvested, washed with PBS, and then lysed in lysis buffer (which was M-PER™ Mammalian Protein Extraction Reagent containing Pierce™ Protease Inhibitor Tablets, Pierce™ Phosphatase Inhibitor Tablets, and 1 mM DTT). Cell lysate was subjected to centrifugation at 14,000 g for 30 min at 4° C. to remove cell debris. The clarified lysate was filtered, and then applied to monomeric avidin-agarose beads. The mixture was subjected to nutation for 24 h at 4° C. The beads were washed (3×) with lysis buffer, and then eluted with lysis buffer containing 2 mM biotin. The eluate was then purified further by chromatography using a 5-mL RNase A-affinity column as described previously (Johnson et al., 2007). The purified, biotinylated RI was stored in storage buffer (which was 20 mM Tris-HCl buffer, pH 7.5, containing 1 mM EDTA, 1 mM DTT, and 50 mM NaCl). The protein sample was then submitted to mass spectrometry at University of Wisconsin Biotechnology Center to identify any sites of phosphorylation.

Immunoblotting and Pull-Down Assay

Cells grown in a 10-cm dish were lysed with 1 mL of M-PER™ Mammalian Protein Extraction Reagent (a mammalian protein extraction reagent that contains a mild, nondenaturing detergent) containing PIERCE™ Protease Inhibitor Tablets (tablets containing protease inhibitors AEBSF, aprotinin, bestatin, E-64, leupeptin, and pepstatin A), PIERCE™ Phosphatase Inhibitor Tablets (sodium fluoride, sodium orthovanadate, sodium pyrophosphate, and beta-glycerophosphate for broad-spectrum inhibition of phosphatase activity), and DTT (1 mM). Cell lysates were subjected to centrifugation for 10 min at 14,000 g to remove cell debris, and the total protein concentration in the supernatant was determined with a Bradford protein assay. Protein (~30 μg) was separated by SDS-PAGE using a gel from Biorad (Hercules, Calif.), and the resulting gel was subjected to transfer to a PVDF membrane with an IBLOT® 2 (a dry transfer device that performs western blotting transfer without the need for liquid buffers) dry transfer system. The membrane was blocked for 1 h in a solution of BSA (5% w/v) in TBS-Tween (TBS-T), washed, and then incubated overnight at 4° C. with an antibody (1:500 dilution) in TBS-T containing BSA (5% w/v). After another wash with TBS-T, membranes were incubated with secondary antibody (1:3000 dilution), washed again, and then detected with an Amersham ECL Select Western Blotting Detection Reagent and by an ImageQuant™ LAS4000 instrument from GE Healthcare (Marlborough, Mass.).

For pull-down assays, after isolation of the total protein, samples were incubated overnight at 4° C. with Streptavidin MAGNESPHERE® (magnetic particles coated with streptavidin) Paramagnetic Particles from Promega. The beads were washed (3×) with PBS containing 1 mM DTT. Samples were eluted with 50 µL of SDS gel-loading dye and processed further for immunoblotting.

Native Gel-Shift Assay

RI was isolated from HEK293T cells and purified further as described above. Unphosphorylated RI (uRI) (3 µM) was prepared by incubating the isolated protein with lambda protein phosphatase from New England BioLabs (Ipswich, Mass.) for 10 min at 37° C., followed by dialysis against PBS containing 1 mM DTT to remove excess phosphatase. RI (or uRI) and the ptRNase were incubated together in a 1:1.3 or 1:1 molar ratio for 20 min at 25° C. to allow for complex formation. A 10-4 aliquot of protein solution was combined with 2 µL of a 6× solution of SDS gel-loading dye, and the resulting mixtures were applied immediately onto a non-denaturing 12% w/v polyacrylamide gel from BioRad. Gels were subjected to electrophoresis in the absence of SDS at 20-25 mA for ~3 h at 4° C. and stained with Coomassie Brilliant Blue G-250 dye.

Protein Thermal Shift Assay

Thermal unfolding of RI (unbound and bound to the ptRNase) was monitored in the presence of a fluorescent dye by using differential scanning fluorimetry (DSF). DSF was performed with a VIIA™ 7 Real-Time PCR machine from Applied Biosystems (Foster City, Calif.). Briefly, a 20-4 solution of protein (10 µM of RI or uRI; 14 nM of the ptRNase) was loaded into the wells of MICROAMP® optical 96-well propylene plate from APPLIED BIOSYSTEMS®, and SYPRO® Orange dye was added to a final dilution of 1:250 in relation to the stock solution from manufacturer. The temperature was increased from 20° C. to 96° C. at 1° C./min in steps of 1° C. Fluorescence intensity was measured at 578 nm, and the denaturation curve was fitted with Protein Thermal Shift™ software from Applied Biosystems to determine values of $T_m$, which is the temperature at the midpoint of the transition.

Calculation of Coulombic Interaction Energies

Calculations were performed on AMD Opteron 2.2-GHz processors running CentOS 6.3 at the Materials and Process Simulation Center of the California Institute of Technology (Pasadena, Calif.). All computational models were based on the crystal structure of the human RI•RNase 1 complex (PDB entry 1z7x), which was determined at 1.95-Å resolution (Johnson et al., 2007). Missing hydrogen atoms were introduced with the program Reduce (version 3.03), and the model was minimized fully (Lovell et al., 1999). All minimizations were carried out to a 0.2 kcal/mol/A RMS-force convergence criterion using conjugate gradient minimization on MPSim in vacuum using forces as described by the DREIDING force-field (Mayo et al., 1990; Lim et al., 1997).

The Coulombic impact of replacing Ser/Thr residues with pSer/pThr on the stability of the RI•RNase 1 complex was calculated as the difference between the energy of the complex and that of its components. Serine and threonine residues at phosphorylation sites were replaced with glutamine, and side-chain conformations of these and other residues within 6 Å were optimized with the program SCREAM (Kam and Goddard, 2008). Following minimization, glutamine side-chains were replaced with pSer or pThr with purpose-written Python (version 2.7) scripts, and the phosphorylated complex was minimized locally. All Coulombic interaction energies reported are relative to that calculated for the wild-type complex.

Similarly, the Coulombic impact of phosphorylation on thiolate formation at cysteine side-chains of RI was calculated through the change in Coulombic interaction energy between a cysteine thiolate and RI upon phosphorylation at a specific site.

Assay of Cell Viability with a Single Drug

Cells in complete growth medium were plated at 5,000 cells per well in a 96-well microplate, which was incubated for 24 h. Cells were then treated with increasing concentrations of each compound, either kinase inhibitors or the ptRNase. After 48 h, the medium was removed, and cells were incubated for 2 h with CellTiter 96® MTS reagent from Promega. Absorbance was recorded on an M1000 fluorimeter from Tecan (Morrisville, N.C.) at 490 nm. Data were analyzed with Prism 5.0 software from GraphPad (La Jolla, Calif.). Values of $EC_{50}$, which is the concentration of a drug that gives half-maximal cell viability, were calculated with the equation:

$$y = y_{min} + \frac{y_{max} - y_{min}}{1 + 10^{(logEC_{50}-x)h}}$$

where y is cell viability, x is the concentration of drug, and h is the Hill coefficient. Data were plotted on a log scale with each data point being the mean of 3 biological replicates.

Assay of Cell Viability with Two Drugs

The $EC_{50}$ values obtained from single-drug cell viability assays were used to design subsequent drug combination experiments. Two-drug combination experiments were performed by using a 5×5 matrix in 96-well plates to interrogate 25 dosing pairs. Cells in complete growth medium were plated at 5,000 cells per well in a 96-well microplate, which was incubated for 24 h at 37° C. Cells were treated with kinase inhibitor for 1 h, followed by the ptRNase. After 48 h, cell viability was evaluated as described above.

The dose-effect curve for each drug was determined based on experimental observations and was compared to the effect afforded by the two-drug combination to derive a CI value. The CI values for all combinations were calculated using CalcuSyn 2.0 from Biosoft (Cambridge, UK). CI<1, CI=1, and CI>1. indicate synergism, an additive effect, and antagonism, respectively. Each CI value was the mean of the results from 3 biological replicates.

Example 2: Treatment of a Subject with Cancer Using the Synergistic Combination of the ptRNase and a MAPK Inhibitor Patients having a solid tumor (e.g., melanoma) are selected and are administered the ptRNase intravenously once weekly for three weeks and repeating treatment every 21 days at a dosage of about 80-200 mg/m² in combination with either trametinib or dabrafenib. Tranetinib is concurrently administered at from 0.5-2 mg orally every day, preferably 2 mg orally every day during treatment. Dabrafenib is administered orally twice a day at 50-150 mg, preferably at 150 mg. Tumor size and progression is monitored.

Some patients receive the ptRNase at 160 mg/m$^2$ in combination with both tranetinib (2 mg orally once a day) and dabrafenib (150 mg orally twice a day).

REFERENCES

Anjum R, Blenis J. 2008. The RSK family of kinases: Emerging roles in cellular signalling. *Nat. Rev. Mol. Cell Biol.* 9:747-758.

Ardelt W, Ardelt B, Darzynkiewicz Z. 2009. Ribonucleases as potential modalities in anticancer therapy. *Eur. J. Pharmacol.* 625:181-189.

Beintema J J, Schuller C, Irie M, Carsana A. 1988. Molecular evolution of the ribonuclease superfamily. *Prog. Biophys. Molec. Biol.* 51:165-192.

Blázquez M, Fominaya J M, Hofsteenge J. 1996. Oxidation of sulfhydryl groups of ribonuclease inhibitor in epithelial cells is sufficient for its intracellular degradation. *J. Biol. Chem.* 271:18638-18642.

Blom N, Gammeltoft S, Brunak S. 1999. Sequence and structure-based prediction of eukaryotic protein phosphorylation sites. *J. Mol. Biol.* 294:1351-1362.

Blom N, Sicheritz-Pontén T, Gupta R, Gammeltoft S, Brunak S. 2004. Prediction of post-translational glycosylation and phosphorylation of proteins from the amino acid sequence. *Proteomics* 4:1633-1649.

Boschelli D H, Ye F, Wang Y D, Dutia M, Johnson S L, Wu B, Miller K, Powell D W, Yaczko D, Young M, Tischler M, Arndt K, Discafani C, Etienne C, Gibbons J, Grod J, Lucas J, Weber J M, Boschelli F. 2001. Optimization of 4-phenylamino-3-quinolinecarbonitriles as potent inhibitors of Src kinase activity. *J. Med. Chem.* 44:3965-3977.

Chao T-Y, Lavis L D, Raines R T. 2010. Cellular uptake of ribonuclease A relies on anionic glycans. *Biochemistry* 49:10666-10673.

Chao T-Y, Raines R T. 2011. Mechanism of ribonuclease A endocytosis: Analogies to cell-penetrating peptides. *Biochemistry* 50:8374-8382.

Cohen P. 2000. The regulation of protein function by multisite phosphorylation—a 25 year update. *Trends Biochem. Sci.* 25:596-601.

Dancey J E, Chen H X. 2006. Strategies for optimizing combinations of molecularly targeted anticancer agents. *Nat. Rev. Drug Discov.* 5:649-659.

Dhillon A S, Hagan S, Rath O, Kolch W. 2007. MAP kinase signalling pathways in cancer. *Oncogene* 26:3279-3290.

Dickson K A, Haigis M C, Raines R T. 2005. Ribonuclease inhibitor: Structure and function. *Prog. Nucleic Acid Res. Mol. Biol.* 80:349-374.

Dickson K A, Kang D-K, Kwon Y S, Kim J C, Leland P A, Kim B-M, Chang S-I, Raines R T. 2009. Ribonuclease inhibitor regulates neovascularization by human angiogenin. *Biochemistry* 48:3804-3806.

Dunn K L, Espino P S, Drobic B, He S, Davie J R. 2005. The Ras-MAPK signal transduction pathway, cancer and chromatin remodeling. *Biochem. Cell Biol.* 83:1-14.

Fang E F, Ng T B. 2011. Ribonucleases of different origins with a wide spectrum of medicinal applications. *Biochim. Biophys. Acta* 1815:65-74.

Ferreras M, Gavilanes J G, López-Otín C, García-Segura J M. 1995. Thiol-disulfide exchange of ribonuclease inhibitor bound to ribonuclease A. *J. Biol. Chem.* 270:28570-28578.

Fett J W, Strydom D J, Lobb R R, Alderman E M, Bethune J L, Riordan J F, Vallee B L. 1985. Isolation and characterization of angiogenin, an angiogenic protein from human carcinoma cells. *Biochemistry* 24:5480-5486.

Fisher B M, Grilley J E, Raines R T. 1998. A new remote subsite in ribonuclease A. *J. Biol. Chem.* 273:34134-34138.

Fominaya J M, Hofsteenge J. 1992. Inactivation of ribonuclease inhibitor by thiol-disulfide exchange. *J. Biol. Chem.* 267:24655-24660.

Fontecilla-Camps J C, de Llorens R, le Du M H, Cuchillo C M. 1994. Crystal structure of ribonuclease A•d(ApTpApApG) complex. *J. Biol. Chem.* 269:21526-21531.

Fry D W, Harvey P J, Keller P R, Elliott W L, Meade M, Trachet E, Albassam M, Zheng X, Leopold W R, Pryer N K, Toogood P L. 2004. Specific inhibition of cyclin-dependent kinase 4/6 by PD 0332991 and associated antitumor activity in human tumor xenografts. *Mol. Cancer Ther.* 3:1427-1438.

Gibson D G, Young L, Chuang R-Y, Venter J C, Hutchinson C A, III, Smith H O. 2009. Enzymatic assembly of DNA molecules up to several hundred kilobases. *Nat. Methods* 6:343-345.

Greger J G, Eastman S D, Zhang V, Bleam M R, Hughes A M, Smieheman K N, Dickerson S H, Laquerre S G, Liu L, Glimer T M. 2012. Combinations of BRAF, MEK, and PI3K/mTOR inhibitors overcome acquired resistance to the BRAF inhibitor GSK2118436 dabrafenib, mediated by NRAS or MEK mutations. *Mol. Cancer Ther.* 11:909-920.

Haigis M C, Haag E S, Raines R T. 2002. Evolution of ribonuclease inhibitor protein by exon duplication. *Mol. Biol. Evol.* 19:960-964.

Haigis M C, Kurten E L, Raines R T. 2003. Ribonuclease inhibitor as an intracellular sentry. *Nucleic Acids Res.* 31:1024-1032.

Hoang T T, Raines R T. 2017. Molecular basis for the autonomous promotion of cell proliferation by angiogenin. *Nucleic Acids Res.* 45:818-831.

Hofsteenge J (1997) Ribonuclease inhibitor. In Ribonucleases: Structures and Functions, D'Alessio G, Riordan J F (eds) pp 621-658. New York: Academic Press.

Johnson L N. 2009. The regulation of protein phosphorylation. *Biochem. Soc. Trans.* 38 (Part 4):627-641.

Johnson R J, McCoy J G, Bingman C A, Phillips G N, Jr., Raines R T. 2007. Inhibition of human pancreatic ribonuclease by the human ribonuclease inhibitor protein. *J. Mol. Biol.* 367:434-449.

Kajava A V. 1998. Structural diversity of leucine-rich repeat proteins. *J. Mol. Biol.* 277:519-527.

Kam V W T, Goddard W A, III. 2008. Flat-bottom strategy for improved accuracy in protein side-chain placements. *J. Chem. Theor. Comput.* 4:2160-2169.

Kefford R, Arkenau H, Brown M P, Millward M, Infante J R, Long G V, Ouellet D, Curtis M, Lebowitz P F, Falchook G S. 2010. Phase I/II study of GSK2118436, a selective inhibitor of oncogenic mutant BRAF kinase, in patients with metastatic melanoma and other solid tumors. *J. Clin. Oncol.* 28 Suppl.:8503.

Kim B-M, Schultz L W, Raines R T. 1999. Variants of ribonuclease inhibitor that resist oxidation. *Protein Sci.* 8:430-434.

King A J, Amone M R, Bleam M R, Moss K G, Yang J, Fedorowicz K E, Smitheman K N, Erhardt J A, Hughes-Earle A, Kane-Carson L S, Sinnamon R H, Qi H, Rheault T R, Uehling D E, Laquerre S G. 2013. Dabrafenib; preclinical characterization, increased efficacy when combined with trametinib, while BRAF/MEK tool combination reduced skin lesions. *PLoS ONE* 8:e67583.

Knight Z A, Shokat K M. 2005. Features of selective kinase inhibitors. *Chem. Biol.* 12:621-637.

Knight Z A, Lin H, Shokat K M. 2010. Targeting the cancer kinome through polypharmacology. *Nat. Rev. Cancer* 10:130-137.

Kobe B, Deisenhofer J. 1993. Crystal structure of porcine ribonuclease inhibitor, a protein with leucine-rich repeats. *Nature* 366:751-756.

Kobe B, Deisenhofer J. 1995. A structural basis of the interactions between leucine-rich repeats and protein ligands. *Nature* 374:183-186.

Kolch W, Heidecker G, Kochs G, Hummel R, Vahidi H, Mischak H, Finkenzeller G, Marmé D, Rapp U R. *Nature* 364:249-252.

Kong A, Kuilman T, Shahrabi A, Boshuizen J, Kemper K, Song J-Y, Niessen H W M, Rozeman E A, Be7ukes-Foppen M H, Blank C U, Peeper D S. 2017. Cancer drug addition is related by an ERK2-dependent phenotype switch. *Nature* 550:270-274.

Lee F S, Vallee B L. 1993. Structure and action of mammalian ribonuclease (angiogenin) inhibitor. *Prog. Nucleic Acid Res. Mol. Biol.* 44:1-30.

Li L, pan X-Y, Shu J, Jiang R, Zhou Y-J, Chen J-X. 2014. Ribonuclease inhibitor up-regulation inhibits the growth and induces apoptosis in murine melanoma cells through repression of angiogenin and ILK/PI3K/AKT signaling pathway. *Biochimie* 103:89-100.

Lim K-T, Brunett S, Iotov M, McClurg R B, Vaidehi N, Dasgupta S, Taylor S, Goddard W A, III. 1997. Molecular dynamics for very large systems on massively parallel computers: The MPSim program. *J. Comput. Chem.* 18:501-521.

Lito P, Solomon M, Li L-S, Hansen R, Rosen N. 2016. Allele-specific inhibitors inactivate mutant KRAS G12C by a trapping mechanism. *Science* 351:604-608.

Lomax J E, Eller C H, Raines R T. 2012. Rational design and evaluation of mammalian ribonuclease cytotoxins. *Methods Enzymol.* 502:273-290.

Lomax J E, Bianchetti C M, Chang A, Phillips G N, Jr., Fox B G, Raines R T. 2014. Functional evolution of ribonuclease inhibitor: Insights from birds and reptiles. *J. Mol. Biol.* 26:3041-3056.

Lomax J E, Eller C H, Raines R T. 2017. Comparative functional analysis of ribonuclease 1 homologs: Molecular insights into evolving vertebrate physiology. *Biochem. J.* 474:2219-2233.

Long G V, Stroyakovskiy D, Gogas H, Levchenko E, de Braud F, Larkin J, Garbe C, Jouary T, Hauschild A, Grob J-J, Chiarion-Sileni V, Lebbe C, Mandala M, Millward M, Hansson J, Utikal J, Ferraresi V, Kovalenko N, Mohr P, Probachai V et al. 2015. Dabrafenib and trametinib versus dabrafenib and placebo for Val600 BRAF-mutant melanoma: A multicentre, double-blind, phase 3 randomised controlled trial. *Lancet* 386:444-451.

Long G V, Hauschild A, Santinami M, Atkinson V, Mandala M, Chiarion-Sileni V, Larkin J, Nyakas M, Dutriaux C, Haydon A, Robert C, Mortier L, Schachter J, Chadendorf D, Lesimple T, Plummer R, Ji R, Zhang P, Mookerjee B, Legos J et al. 2017. Adjuvant dabrafenib plus trametinib in stage III BRAF-mutated melanoma. *N. Eng. J. Med.*: 377:1813-1823; DOI: 10.1056/NEJMoa1708539.

Lopez J S, Banerji U. 2016. Combine and conquer: Challenges for targeted therapy combinations in early phase trials. *Nat. Rev. Clin. Oncol.* 14:57-66.

Lovell J M W S C, Richardson J S, Richardson D C. 1999. Asparagine and glutamine: Using hydrogen atom contacts in the choice of side-chain amide orientation. *J. Mol. Biol.* 285:1735-1747.

Lugowska I, Kosela-Paterczyk H, Kozak K, Rutkowski P. 2015. Trametinib: A MEK inhibitor for management of metastatic melanoma. *Onco. Targets. Ther.* 8:2251-2259.

Lyons S M, Fay M M, Akiyama Y, Anderson P J, Ivanov P. 2017. RNA biology of angiogenin: Current state and perspectives. *RNA Biol.* 14:171-178.

Mayo S L, Olafson B D, Goddard W A, III. 1990. DREIDING: A generic force field for molecular simulations. *J. Phys. Chem.* 94:8897-8909.

McCubrey J A, Steelman L S, Chappell W H, Abrams S L, Wong E W T, Chang F, Lehmann B, Terrian D M, Milella M, Tafuri A, Stivala F, Libra M, Basecke J, Evangelisti C, Martelli A M, Franklin R A. 2007. Roles of the Raf/MEK/ERK pathway in cell growth, malignant transformation and drug resistance. *Biochim. Biophys. Acta* 1773:1263-1284.

Moroianu J, Riordan J F. 1994. Nuclear translocation of angiogenin in proliferating endothelial cells is essential to its angiogenic activity. *Proc. Natl. Acad. Sci. U.S.A.* 91:1677-1681.

Ostrem J M, Shokat K M. 2016. Direct small-molecule inhibitors of KRAS: From structural insights to mechanism-based design. *Nat. Rev. Drug Discov.* 15:771-785.

Papageorgiou A, Shapiro R, Acharya K. 1997. Molecular recognition of human angiogenin by placental ribonuclease inhibitor—an X-ray crystallographic study at 2.0 Å resolution. *EMBO J.* 16:5162-5177.

Patricelli M P, Janes M R, Li L-S, Hansen R, Peters U, Kessler L V, Chen Y, Kucharski J M, Feng J, Ely T, Chen J H, Firdaus S J, Babbar A, Ren P, Liu Y. 2016. Selective inhibition of oncogenic KRAS output with small molecules targeting the inactive state. *Cancer Discov.* 6:316-329.

Pirotte M, Desreux V. 1952. Distribution de la ribonuclease dans les extrait de granules cellulaire du foie. *Bull. Soc. Chim. Belg.* 61:167-180.

Pizzo E, D'Alessio G. 2007. The success of the RNase scaffold in the advance of biosciences and in evolution. *Gene* 406:8-12.

Poole L B. 2015. The basics of thiols and cysteines in redox biology and chemistry. *Free Radic. Biol. Med.* 80:148-157.

Raines R T. 1998. Ribonuclease A. *Chem. Rev.* 98:1045-1065.

Roberts P J, Der C J. 2007. Targeting the Raf-MEK-ERK mitogen-activated protein kinase cascade for the treatment of cancer. *Oncongene* 26:3291-3310.

Roskoski R, Jr. 2012. MEK1/2 dual-specificity protein kinases: Structure and regulation. *Biochem. Biophys. Res. Commun.* 417:5-10.

Roth J S. 1953. Effect of sulphydryl reactants on liver ribonuclease. *Nature* 171:127-128.

Roth J S. 1956. Studies on the properties and distribution of ribonuclease inhibitor in the rat. *Biochim. Biophys. Acta* 21:34-43.

Rutkoski T J, Raines R T. 2008. Evasion of ribonuclease inhibitor as a determinant of ribonuclease cytotoxicity. *Curr. Pharm. Biotechnol.* 9:185-189.

Samatar A A, Poulikakos P I. 2014. Targeting RAS-ERK signalling in cancer: Promises and challenges. *Nat. Rev. Drug Discov.* 13:928-942.

Shapiro R, Vallee B L. 1987. Human placental ribonuclease inhibitor abolishes both angiogenic and ribonucleolytic activities of angiogenin. *Proc. Natl. Acad. Sci. U.S.A.* 84:2238-2241.

Shaul Y D, Seger R. 2007. The MEK/ERK cascade: From signaling specificity to diverse functions. *Biochim. Biophys. Acta* 1773:1213-1226.

Strong L E, Kink J A, Mei B, Shahan M N, Raines R T. 2012a. First in human phase I clinical trial of QBI-139, a human ribonuclease variant, in solid tumors. *J. Clin. Oncol.* 30 (Suppl.): T P S3113.

Strong L E, Kink J A, Pensinger D, Mei B, Shahan M, Raines R T. 2012b. Efficacy of ribonuclease QBI-139 in combination with standard of care therapies. *Cancer Res.* 72 (Suppl. 1):1838.

Thomas S P, Kim E, Kim J-S, Raines R T. 2016. Knockout of the ribonuclease inhibitor gene leaves human cells vulnerable to secretory ribonucleases. *Biochemistry* 55:6359-6362.

Torii S, Yamamoto T, Tsuchiya Y, Nishida E. 2006. ERK MAP kinase in G cell cycle progression and cancer. *Cancer Sci.* 97:697-702.

Vlastaridis P, Kyriakidou P, Chaliotis A, Van de Peer Y, Oliver S G, Amoutzias G D. 2017. Estimating the total number of phosphoprotines and phosphorylation sites in eukaryotic proteomes. *GigaScience* 6:1-11.

Xu Z-p, Tsuji T, Riordan J F, Hu G-f. 2002. The nuclear function of angiogenin in endothelial cells is related to rRNA production. *Biochem. Biophys. Res. Commun.* 294:287-292.

Yamaguchi T, Kakefuda R, Tajima N, Sowa Y, Sakai T. 2011. Antitumor activities of JTP-74057 (GSK1120212), a novel MEK1/2 inhibitor, on colorectal cancer cell lines in vitro and in vivo. *Int. J. Oncol.* 39:23-31.

Zou H Y, Li Q, Lee J H, Arango M E, McDonnell S R, Yamazaki S, Koudriakova T B, Alton G, Cui J J, Kung P-P, Nambu M D, Los G, Bender S L, Mroczkowski B, Christensen J G. 2007. An orally available small-molecule inhibitor of c-Met, PF-2341066, exhibits cytoreductive antitumor efficacy through antiproliferative and antiangiogenic mechanisms. *Cancer Res.* 67:4408-4417.

2.2: Inhibitors Available from Selleckchem or Others

| Inhibitor Name | Target |
|---|---|
| Selumetinib (AZD6244) | MEK1 |
| PD0325901 | MEK |
| Trametinib (GSK1120212) | MEK1/MEK2 |
| U0126-EtOH | MEK1/MEK2 |
| PD184352 (CI-1040) | MEK1/MEK2 |
| PD98059 | MEK1 |
| BIX 02189 | MEK5 |
| Pimasertib (AS-703026) | MEK1/MEK2 |
| BIX 02188 | MEK5 |
| TAK-733 | MEK1 |
| AZD8330 | MEK1/2 |
| Binimetinib (MEK162, ARRY-162, ARRY-438162) | MEK |
| SL-327 | MEK1/MEK2 |
| Refametinib (RDEA119, Bay 86-9766) | MEK1/MEK2 |
| GDC-0623 | MEK1 |
| BI-847325 | MEK1/MEK2 |
| Cobimetinib (GDC-0973, RG7420) | MEK1 |
| PD318088 | MEK1/2 |
| Honokiol | MEK |
| Myricetin | MEK1 |
| K-Ras(G12C) inhibitor 9 | KRAS |
| 6H05 | KRAS (G12C) |
| KRpep-2d | KRAS (G12C) |
| ARS-853 (ARS853) | KRAS (G12C) |
| MRTX849 | KRAS |
| ARS-1620 | KRAS |
| K-Ras (G12C) inhibitor 12 | C-Raf/Raf-1 and B-Raf |
| K-Ras(G12C) inhibitor 6 | C-Raf/Raf-1 and B-Raf |
| Kobe0065 | H-Ras-cRaf1 |
| Vemurafenib (PLX4032, RG7204) | C-Raf/Raf-1 and B-Raf |
| Sorafenib Tosylate | C-Raf/Raf-1 and B-Raf |
| PLX-4720 | C-Raf/Raf-1 and B-Raf |
| Dabrafenib (GSK2118436) | C-Raf/Raf-1 and B-Raf |
| Dabrafenib Mesylate | B-raf/C-Raf |
| GDC-0879 | B-Raf |
| RAF265 (CHIR-265) | B-Raf/C-Raf/ |
| AZ 628 | C-Raf/Raf-1 and B-Raf |
| NVP-BHG712 | C-Raf/Raf-1 |
| SB590885 | B-Raf |
| ZM 336372 | C-Raf/Raf-1 |
| Sorafenib | C-Raf/Raf-1 and B-Raf |
| GW5074 | C-Raf/Raf-1 |
| TAK-632 | C-Raf/Raf-1 and B-Raf |
| CEP-32496 | C-Raf/Raf-1 and B-Raf |
| CCT196969 | C-Raf/Raf-1 and B-Raf |
| LY3009120 | C-Raf/Raf-1 and B-Raf |
| RO5126766 (CH5126766) | C-Raf/Raf-1 and B-Raf and MEK1 |
| LXH254 | C-Raf |
| RAF709 | B-Raf/C-Raf |
| SNS-314 Mesylate | C-Raf |
| Encorafenib (LGX818) | B-Raf |
| PLX7904 | Raf |
| PLX-4720 | B-Raf/C-Raf |
| MLN2480 | Raf |
| SCH772984 | ERK1/ERK2 |
| LY3214996 | ERK1/ERK2 |
| SC1 | ERK1 |
| VX-11e | ERK2 |
| DEL-22379 | ERK5/ERK |
| Ulixertinib (BVD-523, VRT752271) | ERK2 |
| GDC-0994 | ERK1/ERK2 |
| FR 180204 | ERK1/ERK2 |
| ERKS-IN-1 | ERK5 |
| Erlotinib HCl (OSI-744) | EGFR/ErbB1 |
| Gefitinib (ZD1839) | EGFR/ErbB1 |
| Lapatinib (GW-572016) Ditosylate | EGFR/ErbB1 |
| Afatinib (BIBW2992) | EGFR/ErbB1 |
| Neratinib (HKI-272) | EGFR/ErbB1 |
| Canertinib (CI-1033) | EGFR/ErbB1 |
| Lapatinib | EGFR/ErbB1 |
| AG-490 (Tyrphostin B42) | EGFR/ErbB1 |
| Dacomitinib (PF299804, PF299) | EGFR/ErbB1 |
| WZ4002 | EGFR/ErbB1 |
| Sapitinib (AZD8931) | EGFR/ErbB1 |
| CUDC-101 | EGFR/ErbB1 |
| AG-1478 (Tyrphostin AG-1478) | EGFR/ErbB1 |
| PD153035 HCl | EGFR/ErbB1 |
| Pelitinib (EKB-569) | EGFR/ErbB1 |
| AEE788 (NVP-AEE788) | EGFR/ErbB1 |

| Inhibitor Name | Target |
| --- | --- |
| AC480 (BMS-599626) | EGFR/ErbB1 |
| OSI-420 | EGFR/ErbB1 |
| WZ3146 | EGFR/ErbB1 |
| AST-1306 | EGFR/ErbB1 |
| Rociletinib (CO-1686, AVL-301) | EGFR/ErbB1 |
| Varlitinib | EGFR/ErbB1 |
| Icotinib | EGFR/ErbB1 |
| TAK-285 | EGFR/ErbB1 |
| WHI-P154 | EGFR/ErbB1 |
| Daphnetin | EGFR/ErbB1 |
| PD168393 | EGFR/ErbB1 |
| CNX-2006 | EGFR/ErbB1 |
| Tyrphostin 9 | EGFR/ErbB1 |
| AG-18 | EGFR/ErbB1 |
| Cetuximab | EGFR/ErbB1 |
| Nazartinib (EGF816, NVS-816) | EGFR/ErbB1 |
| AZD3759 | EGFR/ErbB1 |
| Afatinib (BIBW2992) Dimaleate | EGFR/ErbB1 |
| Erlotinib | EGFR/ErbB1 |
| CL-387785 (EKI-785) | EGFR/ErbB1 |
| Poziotinib (HM781-36B) | EGFR/ErbB1 |
| Osimertinib (AZD9291) | EGFR/ErbB1 |
| AZ5104 | EGFR/ErbB1 |
| HER2-Inhibitor-1 | EGFR/ErbB1 |
| WZ8040 | EGFR/ErbB1 |
| Genistein | EGFR/ErbB1 |
| Naquotinib(ASP8273) | EGFR/ErbB1 |
| Olmutinib (HM61713, BI 1482694) | EGFR/ErbB1 |
| Butein | EGFR/ErbB1 |
| Chrysophanic Acid | EGFR/ErbB1 |
| Panitumumab | EGFR |
| vandetanib | EGFR |
| Necitumumab | EGFR |
| Lazertinib (YH25448, GNS-1480) | EGFR |
| Norcantharidin | EGFR |
| Avitinib (AC0010) | EGFR |
| EAI045 | EGFR |
| BI-D1870 | RSK1/2/3/4 |
| LJH685 | RSK1/2/3 |
| LJI308 | RSK1/2/3 |
| Sotrastaurin | PKC |
| Staurosporine | PKC |
| Go6976 | PKC |
| Ro 31-8220 Mesylate | PKC |
| Go 6983 | PKC |
| GF109203X | PKC |
| Enzastaurin | PKC |
| (LY317615) | |
| Myricitrin | PKC |
| Bisindolylmaleimide I (GF109203X) | PKC |
| Bisindolylmaleimide IX (Ro 31-8220 Mesylate) | PKC |
| Dequalinium Chloride | PKC |
| Chelerythrine Chloride | PKC |
| Midostaurin (PKC412) | PKC |

```
                                           SEQ ID NO: 1
Lys Glu Ser Arg Ala Lys Lys Phe Gln Arg Gln His
1               5                   10

Met Asp Ser Asp Ser Ser Pro Ser Ser Ser Thr
            15                  20

Tyr Cys Asn Gln Met Met Arg Arg Arg Asn Met Thr
25                  30                  35

Gln Gly Arg Cys Lys Pro Val Asn Thr Phe Val His
                40                  45

Glu Pro Leu Val Asp Val Gln Asn Val Cys Phe Gln
        50                  55                  60

Glu Lys Val Thr Cys Lys Asn Gly Gln Gly Asn Cys
                65                  70

Tyr Lys Ser Asn Ser Ser Met His Ile Thr Asp Cys
        75                  80

Arg Leu Thr Asn Gly Ser Arg Tyr Pro Asn Cys Ala
85                  90                  95

Tyr Arg Thr Ser Pro Lys Glu Arg His Ile Ile Val
                100                 105

Ala Cys Glu Gly Ser Pro Tyr Val Pro Val His Phe
        110                 115                 120

Asp Ala Ser Val Glu Asp Ser Thr
                125
```

Each publication, patent, and patent publication cited in this disclosure is incorporated in reference herein in its entirety. The present invention is not intended to be limited to the foregoing examples, but encompasses all such modifications and variations as come within the scope of the appended claims.

The invention claimed is:

1. A synergistic composition for the treatment of cancer, the composition comprising (1) at least one mitogen-activated protein kinase (MAPK)-pathway inhibitor selected from a mitogen-activated kinase kinase (MEK) inhibitor, an extracellular-signal-regulated kinase (ERK) inhibitor, RAF inhibitor and a RAS inhibitor, and (2) at least one pancreatic-type ribonuclease (ptRNase), wherein the ptRNase is an RNase 1 protein consisting of SEQ ID NO:1 and having mutations selected from the group consisting of G38R/R39G/N67R/N88R RNase 1, R39L/N67L/N88A/G89L/R91L RNase 1, N67D/N88A/G89D/R91D RNase 1, R39D/N88A/G89D/R91D RNase 1, R39D/N67D/G89D/R91D RNase 1, R39D/N67D/N88A/R91D RNase 1, R39D/N67D/N88A/G89D RNase 1, R39D/N67D/N88A/G89D/R91D RNase 1, R4C/G38R/R39D/L86E/N88R/G89D/R91D/V118C RNase 1, R4C/G38R/R39G/N67R/G89R/S9OR/V118C RNase 1, R4C/G38R/R39G/G89R/S9OR/V118C RNase 1, R4C/G38R/R39G/E49R/D53R/N67R/G89R/S9OR/V118C RNase 1, and R4C/G38R/R39G/E49R/D53R/N67R/L86E/N88R/G89D/R91D/V118C RNase 1,
wherein the at least one ptRNase has lower affinity for ribonuclease inhibitor (RI) as compared to the wildtype ptRNase.

2. The synergistic composition of claim 1, wherein the at least one ptRNase is a RI-resistant ptRNase.

3. The synergistic composition of claim 1, wherein at least one MAPK-pathway inhibitor is at least one MEK inhibitor selected from the group consisting of trametinib, selumetinib, binimetinib, cobimetinib, N-[(2R)-2,3-Dihydroxypropoxy]-3,4-difluoro -2-[(2-fluoro-4-iodophenyl)amino]-benzamide (PD-325901), 2-(2-Chloro-4-iodophenylamino)-N -cyclopropylmethoxy-3,4-difluorobenzamide (CI-1040), (R)-N-(2,3-dihydroxypropoxy)-3,4-difluoro-2-(2-fluoro-4-iodophenylamino)benzamide (PD035901), and 3-[(2R)-2,3-dihydroxypropyl]-6-fluoro-5-[(2-fluoro-4-iodophenyl) amino]-8-methyl-pyrido[2,3-d]pyrimidine -4,7(3H,8H)-dione (TAK-733).

4. The synergistic composition of claim 3, wherein at least one MAPK-pathway inhibitor is trametinib or selumetinib.

5. The synergistic composition of claim 1, wherein the at least one MAPK inhibitor comprises at least one BRAF inhibitor selected from the group consisting of dabrafenib (GSK2118436), sorafenib (BAY43-9006), vemurafenib (PLX4032), N-{3-[(5-Chloro -1H-pyrrolo[2,3 -b]pyridin-3 -yl)carb onyl]-2,4-difluorophenyl}-1-propanesulfonamide (PLX 4720), -2-{4-[(1E)-1-(hydroxyimino)-2,3-dihydro-1H-inden-5-yl]-3-(pyridin-4-yl)-1H-pyrazol-1yl}ethan-1-ol (GDC-0879), and encorafenib (LGX818).

6. The synergistic composition of claim 1, wherein the at least one MAPK inhibitor comprises an ERK inhibitor, wherein the ERK inhibitor is selected from the group consisting of 4-[2-(2-chloro-4-fluoroanilino)-5-methylpyrimidin-4-yl]-N-[(1S)-1-(3-chlorophenyl)-2-hydroxyethyl]-1H-pyrrole-2-carboxamide (VTX-1 1 e), (3R)-1-[2-oxo-2-[4-(4-pyrimidin-2-ylphenyl)piperazin-1-yl]ethyl]-N-(3-pyridin-4-yl-1H-indazol-5-yl)pyrrolidine-3-carboxamide (SCH772984), pluripotin (SC1), AEZS-131, 2-(2-amino-3-methoxyphenyl)chromen -4-one (PD98059), 5-(2-phenylpyrazolo[1,5-a]pyridin-3-yl)-2H-pyrazolo[3,4-c]pyridazin-3-amine (FR180204), (5Z)-7-Oxozeaenol (FR148083), ravoxertinib (GDC-0994), ulixertinib, 24[2-Ethoxy-4-(4-hydroxy-1 -piperidinyl)phenyl] amino -5,11-dimethyl-5,11-dihydro-6H-pyrimido[4,5-b][1,4]benzodiazepin-6-one (XMD8-92), 11-Cyclopentyl-2-[[2-ethoxy-4-[[4-(4-methyl-1-piperazinyl)-1-piperidinyl] carbonyl] phenyl]amino]-5,11-dihydro-5-methyl-6H-pyrimido[4,5-b][1,4]benzodiazepin-6-one (ERK5-IN-1), and N-[2,3-Dihydro-3-[(5-methoxy-1H-indol-3-yl)methylene]-2-oxo-1H-indo1-5-yl]-1-piperidinepropanamide (DEL-22379).

7. The synergistic composition of claim 1, wherein the cancer is melanoma.

8. The synergistic composition of claim 7, wherein the melanoma is malignant melanoma.

9. The synergistic composition of claim 1, wherein the cancer is non-small cell lung cancer.

10. The synergistic composition of claim 1, wherein the composition comprises the at least one ptRNase having lower affinity for RI and wherein the at least one MAPK-pathway inhibitor is either trametinib or dabrafenib.

11. The synergistic composition of claim 1, wherein the at least one ptRNase is selected from an RNase 1 protein consisting of SEQ ID NO:1 and having mutations selected from the group consisting of
(a) R4C/G38R/R39D/L86E/N88R/G89D/R91D/V118C RNase 1,
(b) R4C/G38R/R39G/N67R/G89R/S90R/V118C RNase 1,
(c) R4C/G38R/R39G/G89R/S90R/V118C RNase 1,
(d) R4C/G38R/R39G/E49R/D53R/N67R/G89R/S90R/V118C RNase 1, and
(e) R4C/G38R/R39G/E49R/D53R/N67R/L86E/N88R/G89D/R91D/V118C RNase 1, wherein the at least one ptRNase has lower affinity for ribonuclease inhibitor (RI) as compared to the wildtype ptRNase.

12. The synergistic composition of claim 11, wherein the at least one ptRNase is R4C/G38R/R39G/N67R/G89R/S90R/V118C RNase 1, wherein the at least one ptRNase has lower affinity for ribonuclease inhibitor (RI) as compared to the wildtype ptRNase.

13. The synergistic composition of claim 1, wherein the at least one ptRNase is selected from an RNase 1 protein consisting of SEQ ID NO:1 and having mutations selected from the group consisting of: (a) G38R/R39G/N67R/N88R RNase 1, (b) R39L/N67L/N88A/G89L/R91L RNase 1,
(c) N67D/N88A /G89D/R91D RNase 1, (d) R39D/N88A/G89D/R91D RNase 1,
(e) R39D/N67D /G89D/R91D RNase 1, (f) R39D/N67D/N88A/R91D RNase 1,
(g) R39D/N67D /N88A/G89D RNase 1, (h) R39D/N67D/N88A/G89D/R91D RNase 1,
(i) R4C/G38R/R39D/L86E/N88R/G89D/R91D/V118C RNase 1, and
(j) R4C/G38R/R39G/N67R/G89R/S9OR/V118C RNase 1, wherein the at least one ptRNase has lower affinity for ribonuclease inhibitor (RI) as compared to the wildtype ptRNase.

14. A method of treating cancer in a subject comprising administering to the subject a therapeutically effective amount of the composition of claim 1.

15. The method of claim 14 wherein the at least one MAPK-pathway inhibitor and the at least one ptRNase of the synergistic composition are administered concurrently or sequentially.

16. The method of claim 14, wherein the cancer is selected from melanoma, non-small cell lung cancer, squamous cell carcinoma of the head and neck, ovarian cancer, pancreatic cancer, renal cell carcinoma, hepatocellular carcinoma, bladder cancer, malignant glioma, colorectal cancer, and endometrial cancer.

17. The method of claim 14, wherein administration of the combination of at least one MAPK-pathway inhibitor and at least one cytotoxic ptRNAase results in synergistic inhibition of cancer growth.

18. A method of reducing or inhibiting cancer cell growth in a subject having cancer, the method comprising administering an effective amount of the synergistic composition of claim 1, wherein cancer cell growth is reduced or inhibited in the subject.

19. The method of claim 18, wherein the cancer is selected from melanoma, non-small cell lung cancer, squamous cell carcinoma of the head and neck, ovarian cancer, pancreatic cancer, renal cell carcinoma, hepatocellular carcinoma, bladder cancer, malignant glioma, colorectal cancer, and endometrial cancer.

20. The method of claim 18, wherein the administration of the synergistic combination results in synergistic inhibition of cancer cell growth.

21. The method of claim 18, wherein the cancer is metastatic.

22. The method of claim 18, wherein the at least one MAPK-pathway inhibitor and the at least one ptRNase of the synergistic composition are administered concurrently or sequentially.

23. The method of claim 1, wherein the cancer comprises a cancer or tumor having cells that exhibit ERK-pathway activation or cells that exhibit up-regulation of the RAF-MEK-ERK pathway.

24. The method of claim 14, wherein the ERK-pathway activation in the cancer can result from a mutation in KRAS; a mutation in NRAS; a mutation in HRAS; a mutation in ARAF; a mutation in BRAF; a mutation in CRAF; a mutation in MAP2K1 (MEK1); loss of NF1 function due to mutation, deletion, and/or promoter methylation; and activation of RAS by cell-surface receptors.

25. The method of claim 14, wherein the cancer comprises cells expressing a mutation in at least one of BRAF, MEK, or KRAS.

26. The method of claim 14, wherein the cancer is a $BRAF^{v600E/K}$ mutation-positive unresectable or metastatic melanoma.

* * * * *

UNITED STATES PATENT AND TRADEMARK OFFICE
CERTIFICATE OF CORRECTION

PATENT NO. : 11,286,469 B2
APPLICATION NO. : 16/184629
DATED : March 29, 2022
INVENTOR(S) : Ronald T. Raines et al.

It is certified that error appears in the above-identified patent and that said Letters Patent is hereby corrected as shown below:

In the Specification

Column 2, Line 2, "rote" should be --role--.

Column 5, Line 3, "Motinylated" should be --Botinylated--.

Column 19, Line 30, "10-4 aliquot" should be --10-µL aliquot--.

Column 19, Line 42, "20-4 solution" should be --20-µL solution--.

Column 19, Line 43, "14 nM" should be --14 µM--.

In the Claims

Column 31, Line 46, "R4C/G38R/R39G/N67R/G89R/S9OR/V1186" should be --R4C/G38R/R39G/N67R/G89R/S90R/V118--.

Column 31, Line 47, "R4C/G38R/R39G/G89R/S9OR/V118C" should be --R4C/G38R/R39G/G89R/S90R/V118C--.

Column 31, Line 49, "S9OR/V118C" should be --S90R/V118C--.

Column 32, Line 37, "carb onyl]-2," should be --carbonyl]-2,--.

Column 33, Line 37, "R4C/G38R/R39G/N67R/G89R/S9OR/V118C" should be --R4C/G38R/R39G/N67R/G89R/S90R/V118C--.

Signed and Sealed this
Twentieth Day of August, 2024

Katherine Kelly Vidal
*Director of the United States Patent and Trademark Office*

SEQUENCE LISTING

<160> NUMBER OF SEQ ID NOS: 5

<210> SEQ ID NO 1
<211> LENGTH: 218
<212> TYPE: PRT
<213> ORGANISM: Artificial Sequence
<220> FEATURE:
<223> OTHER INFORMATION: synthetic

<400> SEQUENCE: 1

Gly Arg Arg Gly Asn Arg Asn Arg Arg Asn Ala Ser Glu Arg Asp Asn
1               5                   10                  15

Asp Asn Ala Gly Asp Arg Asp Arg Asn Ala Ser Glu Arg Leu Asn Leu
            20                  25                  30

Asn Ala Gly Leu Arg Leu Arg Asn Ala Ser Glu Asn Asp Asn Ala Gly

```
                    35                  40                  45
Asp Arg Asp Arg Asn Ala Ser Glu Arg Asp Asn Ala Gly Asp Arg Asp
    50                  55                  60
Arg Asn Ala Ser Glu Arg Asp Asn Asp Gly Asp Arg Asp Arg Asn Ala
65                  70                  75                  80
Ser Glu Arg Asp Asn Asp Ala Arg Asp Arg Asn Ala Ser Glu Arg
                85                  90                  95
Asp Asn Asp Asn Ala Gly Asp Arg Asn Ala Ser Glu Arg Cys Gly Arg
                100                 105                 110
Arg Asp Leu Glu Asn Arg Gly Asp Arg Asp Val Cys Arg Asn Ala Ser
            115                 120                 125
Glu Arg Cys Gly Arg Arg Gly Asn Arg Gly Arg Ser Arg Val Cys Arg
            130                 135                 140
Asn Ala Ser Glu Arg Cys Gly Arg Gly Gly Arg Ser Arg Val Cys
145                 150                 155                 160
Arg Asn Ala Ser Glu Arg Cys Gly Arg Gly Glu Arg Asp Arg Asn
                165                 170                 175
Arg Gly Arg Ser Arg Val Cys Arg Asn Ala Ser Glu Ala Asn Asp Arg
                180                 185                 190
Cys Gly Arg Arg Gly Glu Arg Asp Arg Asn Arg Leu Glu Asn Arg Gly
                195                 200                 205
Asp Arg Asp Val Cys Arg Asn Ala Ser Glu
    210                 215

<210> SEQ ID NO 2
<211> LENGTH: 36
<212> TYPE: PRT
<213> ORGANISM: Artificial Sequence
<220> FEATURE:
<223> OTHER INFORMATION: synthetic

<400> SEQUENCE: 2

Lys Glu Val Thr Val Ser Asn Asn Asp Ile Asn Glu Ser Leu Lys Glu
1               5                   10                  15
Leu Ser Leu Ala Gly Asn Glu Leu Arg Glu Leu Asp Leu Ser Asn Asn
            20                  25                  30
Cys Leu Gly Asp
        35

<210> SEQ ID NO 3
<211> LENGTH: 36
<212> TYPE: PRT
<213> ORGANISM: Artificial Sequence
<220> FEATURE:
<223> OTHER INFORMATION: synthetic

<400> SEQUENCE: 3

Lys Glu Leu Val Leu Ser Asn Asn Asp Leu His Glu Ser Leu Lys Glu
1               5                   10                  15
Leu Ser Leu Ala Ser Asn Glu Leu Lys Glu Leu Asp Leu Ser Asn Asn
            20                  25                  30
Cys Met Gly Gly
        35

<210> SEQ ID NO 4
<211> LENGTH: 36
<212> TYPE: PRT
<213> ORGANISM: Artificial Sequence
<220> FEATURE:
```

```
<223> OTHER INFORMATION: synthetic

<400> SEQUENCE: 4

Lys Glu Leu Val Leu Ser Asn Asn Asp Phe His Glu Ser Leu Lys Glu
1               5                   10                  15

Leu Ser Leu Ala Gly Asn Glu Leu Arg Glu Leu Asp Leu Ser Asn Asn
            20                  25                  30

Cys Met Gly Asp
        35

<210> SEQ ID NO 5
<211> LENGTH: 36
<212> TYPE: PRT
<213> ORGANISM: Artificial Sequence
<220> FEATURE:
<223> OTHER INFORMATION: synthetic

<400> SEQUENCE: 5

Lys Glu Leu Thr Val Ser Asn Asn Asp Ile Gly Glu Thr Leu Lys Glu
1               5                   10                  15

Leu Ser Leu Ala Gly Asn Lys Leu Arg Glu Leu Asp Leu Ser Asn Asn
            20                  25                  30

Cys Val Gly Asp
        35
```